(12) United States Patent
Dumas et al.

(10) Patent No.: US 7,678,811 B2
(45) Date of Patent: Mar. 16, 2010

(54) PYRIDINE, QUINOLINE, AND ISOQUINOLINE N-OXIDES AS KINASE INHIBITORS

(75) Inventors: Jacques Dumas, Bethany, CT (US); William J. Scott, Guilford, CT (US); Bernd Riedl, Wuppertal (DE)

(73) Assignee: Bayer Healthcare LLC, Tarrytown, NY (US)

( * ) Notice: Subject to any disclaimer, the term of this patent is extended or adjusted under 35 U.S.C. 154(b) by 96 days.

(21) Appl. No.: 11/775,457

(22) Filed: Jul. 10, 2007

(65) Prior Publication Data

US 2007/0265315 A1    Nov. 15, 2007

Related U.S. Application Data

(63) Continuation of application No. 10/361,850, filed on Feb. 11, 2003, now abandoned.

(60) Provisional application No. 60/354,935, filed on Feb. 11, 2002.

(51) Int. Cl.
C07D 401/02 (2006.01)
A61K 31/44 (2006.01)
A61K 31/47 (2006.01)

(52) U.S. Cl. ............... 514/307; 514/314; 514/332; 514/345; 514/352; 514/354; 546/143; 546/159; 546/255; 546/290; 546/304

(58) Field of Classification Search ............. None
See application file for complete search history.

(56) References Cited

U.S. PATENT DOCUMENTS

| | | |
|---|---|---|
| 502,504 A | 8/1893 | Thoms |
| 1,792,156 A | 2/1931 | Fitzky |
| 2,046,375 A | 7/1936 | Goldstein et al. |
| 2,093,265 A | 9/1937 | Coffey et al. |
| 2,288,422 A | 6/1942 | Rohm et al. |
| 2,649,476 A | 8/1953 | Martin |
| 2,683,082 A | 7/1954 | Hill et al. |
| 2,722,544 A | 11/1955 | Martin |
| 2,745,874 A | 5/1956 | Schetty et al. |
| 2,781,330 A | 2/1957 | Downey |
| 2,797,214 A | 6/1957 | Bossard |
| 2,867,659 A | 1/1959 | Model et al. |
| 2,877,268 A | 3/1959 | Applegath et al. |
| 2,960,488 A | 11/1960 | Tamblyn et al. |
| 2,973,386 A | 2/1961 | Weldon |
| 3,151,023 A | 9/1964 | Martin |
| 3,200,035 A | 8/1965 | Martin et al. |
| 3,230,141 A | 1/1966 | Frick et al. |
| 3,424,760 A | 1/1969 | Helsley et al. |
| 3,424,761 A | 1/1969 | Helsley et al. |
| 3,424,762 A | 1/1969 | Helsley et al. |
| 3,547,940 A | 12/1970 | Brantley |
| 3,646,059 A | 2/1972 | Brantley |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 3,860,645 A | 1/1975 | Nikawitz |
| 3,990,879 A | 11/1976 | Soper |
| 4,001,256 A | 1/1977 | Callahan et al. |
| 4,009,847 A | 3/1977 | Aldrich et al. |
| 4,042,372 A | 8/1977 | Harper |
| 4,062,861 A | 12/1977 | Yukinaga et al. |
| 4,071,524 A | 1/1978 | Banitt |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,279,639 A | 7/1981 | Okamoto et al. |
| 4,405,644 A | 9/1983 | Kabbe et al. |
| 4,410,697 A | 10/1983 | Török et al. |
| 4,437,878 A | 3/1984 | Acker et al. |

(Continued)

FOREIGN PATENT DOCUMENTS

CN    2 146 707    10/1995

(Continued)

OTHER PUBLICATIONS

Audia, James E., et al., "Potent, Selective Tetrahydro-β-carboline Antagonists of the Serotonin 2B (5HT$_{29}$) Contractile Receptor in the Rat Stomach Fundus" J. Med. Chem. 1996, 39, pp. 2773-2780.

(Continued)

*Primary Examiner*—Zinna N Davis
(74) *Attorney, Agent, or Firm*—Millen, White, Zelano & Branigan, P.C.

(57) ABSTRACT

This invention relates to urea compounds containing a pyridine, quinoline, or isoquinoline functionality which is oxidized at the nitrogen heteroatom and which are useful in the treatment of (i) raf mediated diseases, for example, cancer, (ii) p38 mediated diseases such as inflammation and osteoporosis, and (iii) VEGF mediated diseases such as angogenesis disorders.

17 Claims, No Drawings

U.S. PATENT DOCUMENTS

| | | | |
|---|---|---|---|
| 4,468,380 A | 8/1984 | O'Doherty et al. |
| 4,473,579 A | 9/1984 | Devries et al. |
| 4,511,571 A | 4/1985 | Böger et al. |
| 4,514,571 A | 4/1985 | Nakai et al. |
| 4,526,997 A | 7/1985 | O'Doherty et al. |
| 4,623,662 A | 11/1986 | DeVries et al. |
| 4,643,849 A | 2/1987 | Hirai et al. |
| 4,740,520 A | 4/1988 | Hallenbach et al. |
| 4,760,063 A | 7/1988 | Hallenbach et al. |
| 4,808,588 A | 2/1989 | King |
| 4,820,871 A | 4/1989 | Kissener et al. |
| 4,863,924 A | 9/1989 | Haga et al. |
| 4,973,675 A | 11/1990 | Israel et al. |
| 4,983,605 A | 1/1991 | Kondo et al. |
| 4,985,449 A | 1/1991 | Haga et al. |
| 5,036,072 A | 7/1991 | Nakajima et al. |
| 5,059,614 A | 10/1991 | Lepage et al. |
| 5,063,247 A | 11/1991 | Sekiya et al. |
| 5,098,907 A | 3/1992 | Kondo et al. |
| 5,130,331 A | 7/1992 | Pascual |
| 5,151,344 A | 9/1992 | Abe et al. |
| 5,162,360 A | 11/1992 | Creswell et al. |
| 5,185,358 A | 2/1993 | Creswell et al. |
| 5,312,820 A | 5/1994 | Ashton et al. |
| 5,319,099 A | 6/1994 | Kamata et al. |
| 5,399,566 A | 3/1995 | Katano et al. |
| 5,423,905 A | 6/1995 | Fringeli |
| 5,429,918 A | 7/1995 | Seto et al. |
| 5,447,957 A | 9/1995 | Adams et al. |
| 5,470,882 A | 11/1995 | Dixon et al. |
| 5,500,424 A | 3/1996 | Nagamine et al. |
| 5,508,288 A | 4/1996 | Forbes et al. |
| 5,559,137 A | 9/1996 | Adams et al. |
| 5,596,001 A | 1/1997 | Hamanaka |
| 5,597,719 A | 1/1997 | Freed et al. |
| 5,658,903 A | 8/1997 | Adams et al. |
| 5,696,138 A | 12/1997 | Olesen et al. |
| 5,698,581 A | 12/1997 | Kleemann et al. |
| 5,710,094 A | 1/1998 | Minami et al. |
| 5,773,459 A | 6/1998 | Tang et al. |
| 5,780,483 A | 7/1998 | Widdowson et al. |
| 5,807,891 A | 9/1998 | Bold et al. |
| 5,808,080 A | 9/1998 | Bell et al. |
| 5,814,646 A | 9/1998 | Heinz et al. |
| 5,886,044 A | 3/1999 | Widdowson et al. |
| 5,891,895 A | 4/1999 | Shiraishi et al. |
| 5,908,865 A | 6/1999 | Doi et al. |
| 5,929,250 A | 7/1999 | Widdowson et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,020,345 A | 2/2000 | Vacher et al. |
| 6,022,884 A | 2/2000 | Mantlo et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,133,319 A | 10/2000 | Widdowson |
| 6,143,764 A | 11/2000 | Kubo et al. |
| 6,147,116 A | 11/2000 | Barbachyn et al. |
| 6,150,415 A | 11/2000 | Hammock et al. |
| 6,174,901 B1 | 1/2001 | Mantlo et al. |
| 6,178,399 B1 | 1/2001 | Takebayashi et al. |
| 6,180,675 B1 | 1/2001 | Widdowson et al. |
| 6,187,799 B1 | 2/2001 | Wood et al. |
| 6,211,373 B1 | 4/2001 | Widdowson et al. |
| 6,218,539 B1 | 4/2001 | Widdowson |
| 6,242,601 B1 | 6/2001 | Breu et al. |
| 6,262,113 B1 | 7/2001 | Widdowson et al. |
| 6,271,261 B1 | 8/2001 | Widdowson |
| 6,297,381 B1 | 10/2001 | Cirillo et al. |
| 6,310,068 B1 | 10/2001 | Böttcher et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,358,945 B1 | 3/2002 | Breitfelder et al. |
| 6,372,773 B1 | 4/2002 | Regan |
| 6,391,917 B1 | 5/2002 | Petrie et al. |
| 6,492,393 B1 | 12/2002 | Breitfelder et al. |
| 6,525,046 B1 | 2/2003 | Cirillo et al. |
| 6,583,282 B1 | 6/2003 | Zhang et al. |
| 6,608,052 B2 | 8/2003 | Breitfelder et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2002/0042517 A1 | 4/2002 | Uday et al. |
| 2002/0062763 A1 | 5/2002 | Macholdt et al. |
| 2002/0065283 A1 | 5/2002 | McMahon et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0128321 A1 | 9/2002 | Widdowson et al. |
| 2002/0137774 A1 | 9/2002 | Riedl et al. |
| 2002/0017507 A1 | 11/2002 | Santora et al. |
| 2002/0165394 A1 | 11/2002 | Dumas et al. |
| 2004/0209905 A1 | 10/2004 | Kubo et al. |

FOREIGN PATENT DOCUMENTS

| | | |
|---|---|---|
| DE | 487 014 | 11/1929 |
| DE | 511 468 | 10/1930 |
| DE | 523 437 | 4/1931 |
| DE | 2436179 C2 | 2/1975 |
| DE | 25 01 648 A1 | 7/1975 |
| DE | 2436179 A1 | 10/1981 |
| DE | 3305866 A1 | 8/1984 |
| DE | 35 29 247 A1 | 2/1987 |
| DE | 35 40 377 A1 | 5/1987 |
| DE | 253997 A1 | 2/1988 |
| EP | 0016371 A1 | 10/1980 |
| EP | 0107214 A2 | 9/1983 |
| EP | 0116932 A1 | 8/1984 |
| EP | 0192263 B1 | 8/1986 |
| EP | 0202538 A1 | 11/1986 |
| EP | 0230400 A2 | 7/1987 |
| EP | 0233559 B1 | 8/1987 |
| EP | 0242666 A1 | 10/1987 |
| EP | 0264904 A2 | 4/1988 |
| EP | 0335156 A1 | 10/1989 |
| EP | 0359148 A1 | 3/1990 |
| EP | 0371876 A1 | 6/1990 |
| EP | 0379915 A1 | 8/1990 |
| EP | 0380048 A2 | 8/1990 |
| EP | 0381987 A1 | 8/1990 |
| EP | 0405233 A1 | 1/1991 |
| EP | 0425443 A1 | 5/1991 |
| EP | 04599887 | 12/1991 |
| EP | 0676395 | 10/1995 |
| EP | 0709225 B1 | 8/1998 |
| EP | 0860433 A1 | 8/1998 |
| EP | 1199306 A1 | 4/2002 |
| EP | 1256587 A1 | 11/2002 |
| FR | 1 457 172 | 9/1966 |
| GB | 828 231 | 10/1956 |
| GB | 771 333 | 3/1957 |
| GB | 921 682 | 3/1963 |
| GB | 1110099 | 6/1966 |

| | | | | | | |
|---|---|---|---|---|---|---|
| GB | 1 590 870 | 6/1981 | | WO | 99/32436 | 7/1999 |
| IR | 26555 | 1/2000 | | WO | 99/32437 | 7/1999 |
| JP | 44 2569 | 2/1944 | | WO | 99/32455 | 7/1999 |
| JP | 50-76072 | 6/1975 | | WO | 99/32463 | 7/1999 |
| JP | 50-77375 | 6/1975 | | WO | 99/33458 | 7/1999 |
| JP | 50-149668 | 11/1975 | | WO | WO 99/62890 A1 | 12/1999 |
| JP | 51-63170 | 6/1976 | | WO | WO 9962890 A1 | 12/1999 |
| JP | 51-80862 | 7/1976 | | WO | 00/17175 | 3/2000 |
| JP | 53-86033 | 7/1978 | | WO | WO 0026203 A1 | 5/2000 |
| JP | 54-032468 | 9/1979 | | WO | WO 0035454 A1 | 6/2000 |
| JP | 55-98152 | 7/1980 | | WO | 00/41698 | 7/2000 |
| JP | 55-124763 | 9/1980 | | WO | 00/42012 | 7/2000 |
| JP | 55-162772 | 12/1980 | | WO | 00/43366 | 7/2000 |
| JP | 61020039 A2 | 7/1984 | | WO | 00/43384 | 7/2000 |
| JP | 02035450 A2 | 7/1988 | | WO | WO 0043366 A1 | 7/2000 |
| JP | 06075172 B4 | 9/1988 | | WO | 00/47577 | 8/2000 |
| JP | 01009455 A2 | 1/1989 | | WO | 00/50425 A1 | 8/2000 |
| JP | 01102461 A2 | 4/1989 | | WO | WO 0050425 A1 | 8/2000 |
| JP | 01200254 A2 | 8/1989 | | WO | 00/55139 | 9/2000 |
| JP | 01259360 A2 | 10/1989 | | WO | 00/55152 | 9/2000 |
| JP | 03198049 A2 | 12/1989 | | WO | 00/56331 | 9/2000 |
| JP | 02105016 A2 | 4/1990 | | WO | WO 0055152 A1 | 9/2000 |
| JP | 02108048 A2 | 4/1990 | | WO | WO 0056331 A1 | 9/2000 |
| JP | 02150840 A2 | 6/1990 | | WO | WO 0071532 A1 | 11/2000 |
| JP | 3 532 47 | 3/1991 | | WO | 01/04115 A2 | 1/2001 |
| JP | 03144634 A2 | 6/1991 | | WO | WO 01/04115 A2 | 1/2001 |
| JP | 06120039 A2 | 10/1992 | | WO | WO 0104115 A2 | 1/2001 |
| JP | 08-301841 | 11/1996 | | WO | 01/09088 A1 | 2/2001 |
| JP | 10-306078 | 11/1998 | | WO | WO 01/07411 A1 | 2/2001 |
| LB | 6124 | 1/2000 | | WO | WO 0107411 A1 | 2/2001 |
| WO | 90/02112 | 3/1990 | | WO | WO 0109088 A1 | 2/2001 |
| WO | WO 9203413 A1 | 3/1992 | | WO | 01/36403 A1 | 5/2001 |
| WO | 93/18028 | 9/1993 | | WO | WO 0157008 A1 | 8/2001 |
| WO | 93/24458 | 12/1993 | | WO | WO 02/07772 A2 | 1/2002 |
| WO | 94/14801 | 7/1994 | | WO | WO 02/14311 A2 | 2/2002 |
| WO | 94/18170 | 8/1994 | | WO | WO 0210141 A1 | 2/2002 |
| WO | 94/22807 | 10/1994 | | WO | WO 0214281 A1 | 2/2002 |
| WO | 94/25012 | 11/1994 | | WO | 02/24635 A2 | 3/2002 |
| WO | 95/02591 | 1/1995 | | WO | WO 0218346 A1 | 3/2002 |
| WO | 95/07922 | 3/1995 | | WO | WO 02/32872 A1 | 4/2002 |
| WO | 95/13067 | 5/1995 | | WO | WO 02/44158 A1 | 6/2002 |
| WO | 95/31451 | 11/1995 | | WO | 02/059102 A2 | 8/2002 |
| WO | 95/33458 | 12/1995 | | WO | 02/062763 A2 | 8/2002 |
| WO | 96/10559 | 4/1996 | | WO | WO 02059081 A2 | 8/2002 |
| WO | 96/13632 | 5/1996 | | WO | WO 02059102 A2 | 8/2002 |
| WO | 96/25157 | 8/1996 | | WO | 02/083628 A1 | 10/2002 |
| WO | 96/40673 | 12/1996 | | WO | 02/085857 A2 | 10/2002 |
| WO | 96/40675 | 12/1996 | | WO | 02/085859 A1 | 10/2002 |
| WO | 97/09973 A2 | 3/1997 | | WO | WO 02083628 A1 | 10/2002 |
| WO | 97/17329 | 5/1997 | | WO | WO 02083642 A1 | 10/2002 |
| WO | 97/29743 | 8/1997 | | WO | WO 03047523 A2 | 6/2003 |
| WO | 97/30992 | 8/1997 | | WO | 03/068229 A1 | 8/2003 |
| WO | 97/40028 | 10/1997 | | WO | 03/068746 A1 | 8/2003 |
| WO | 97/45400 | 12/1997 | | WO | WO 03068228 A1 | 8/2003 |
| WO | 97/49399 | 12/1997 | | WO | 03/082272 A1 | 10/2003 |
| WO | 97/49400 | 12/1997 | | WO | 03/099771 A2 | 12/2003 |
| WO | 98/17267 | 4/1998 | | WO | WO 2004019941 A1 | 3/2004 |
| WO | 98/22103 | 5/1998 | | WO | WO 2004037789 A2 | 5/2004 |
| WO | 98/22432 | 5/1998 | | WO | WO 2004043374 A2 | 5/2004 |
| WO | WO 9820868 A1 | 5/1998 | | WO | WO 2004078746 A2 | 9/2004 |
| WO | 98/32439 A1 | 7/1998 | | WO | WO 2004085399 A1 | 10/2004 |
| WO | 98/34929 A1 | 8/1998 | | WO | WO 2004085425 A1 | 10/2004 |
| WO | 98/52558 | 11/1998 | | WO | WO 2005002673 A1 | 1/2005 |
| WO | 98/52559 | 11/1998 | | WO | WO 2005004863 A1 | 1/2005 |
| WO | 99/00357 | 1/1999 | | WO | WO 2005004864 A1 | 1/2005 |
| WO | 99/00370 | 1/1999 | | WO | WO 2005005389 A2 | 1/2005 |
| WO | 99/20617 | 4/1999 | | WO | WO 2005019192 A1 | 3/2005 |
| WO | 99/21835 | 5/1999 | | WO | WO 2005032548 A1 | 4/2005 |
| WO | 99/23091 | 5/1999 | | WO | WO 2005037273 A1 | 4/2005 |
| WO | 99/24398 | 5/1999 | | WO | WO 2005037285 A1 | 4/2005 |
| WO | 99/32106 | 7/1999 | | WO | WO 2005037829 A1 | 4/2005 |
| WO | 99/32110 | 7/1999 | | WO | WO 2005042520 A1 | 5/2005 |
| WO | 99/32111 | 7/1999 | | WO | WO 2005047283 A1 | 5/2005 |

| WO | 2005/048948 | A2 | 6/2005 |
| WO | WO 2005048948 | A2 | 6/2005 |
| WO | WO 2005049603 | A1 | 6/2005 |
| WO | WO 2005058832 | A1 | 6/2005 |

OTHER PUBLICATIONS

Forbes, Ian T., "N-(1-Methyl-5-indolyl)-N'-(3-methyl-5-isothiazolyl)urea: A Novel, High-Affinity 5-HT$_{2B}$ Receptor Antagonist", Journal of Medicinal Chem. vol. 38, No. 6, Mar. 17, 1995, pp. 855-857.
Boulton A. J., et al., "Heterocyclic Rearrangements. Part X,[1] A Generalised Monocyclic Rearrangement", J. Chem. Soc. (C), 1967, pp. 2005-2007.
W. Kolch, et al., "Raf-1 protein kinase is required for growth of induced NIH/3T3 cells", Letters to Nature, vol. 349, Jan. 31, 1991, pp. 426-428.
M. Fridman, et al., "The Minimal Fragments of c-Raf-1 and NF1 That Can Suppress v-Ha-Ras-Induced Malignant Phenotype", The Journal of Biological Chemistry, vol. 269, No. 48, Dec. 2, 1994, pp. 30105-30108.
G. L. Bolton, et al., Chapter 17. Ras Oncogene Directed Approaches in Cancer Chemotherapy, Annual Reports in Medicinal Chemistry, vol. 29, 1994, pp. 165-174.
J. L. Bos, "ras Oncogenes in Human Cancer: A Review", Cancer Research, vol. 49, Sep. 1, 1989, pp. 4682-4689.
Michaelis, Justus, Liebigs Ann. Chem. (JLACBF) 397, 1913, 143.
B. P. Monia et al., "Antitumor activity of a phosphorothioate antisense oligodeoxynucleotide targeted against C-raf kinase", Nature Medicine, vol. 2, No. 6, Jun. 1996, pp. 668-675.
Lee, et al., Bicyclic Imidazoles as a Novel Class of Cytokine Biosynthesis Inhibitors, Annuals N.Y. Academy of Science, 1993, pp. 149-170.
F. Lepage, et al., "New N-aryl isoxazolecarboxamides and N-isoxazolybenzamides as anticonvulsant agents", Eur. J. Med. Chem, vol. 27, 1992, pp. 581-593.
Ridley, et al., "Actions of IL-1 are Selectively Controlled by p38 Mitogen-Activated Protein Kinase", The American Association of Immunologists, 1997, p. 3165-73.
N. S. Magnuson, et al., "The Raf-1 serine/threonine protein kinase", Cancer Biology, vol. 5, 1994, pp. 247-253.
G. Daum, et al., "The ins and outs of Raf Kinases",: TIBS 19, Nov. 1994, pp. 474-480.
Grant, A.M. et al.: "Hypotensive thiadiazoles", J. Med. Chem. (1972), 15(10), p. 1082-4.
Russo, F. et al., "Synthesis of 2,6-substituted derivatives of 5H-1,3,4-thiadiazolo=3,2-al-s triazine-5,7-dione" Farmaco, Ed.Sci. (1978), 33(12), 972-83.
Joseph T. Bruder et al., Journal of Virology, Jan. 1997, "Adenovirus Infection Stimulates the Raf/MAPK Signaling Pathway and Induces Interleukin-8 Expression", May 17, 1996, pp. 398-404.
Foussard-Blanpin, Odette: "Comparative phamacodynamic study of variously substituted carboxamides of the central nervous ststem" Ann. Pharm. Fr. (1982), 40 (4), pp. 339-350.
Kubo, Hiroshi et al., vol. 18, No. 1, Jan.-Feb. 1970 "Herbicidal activity of 1,3,4-thiadiazole derivatives" J. Agr. Food Chem. (1970), 18(1), pp. 60-65.
Avruch et al., "Raf meets Ras: completing the framework of a signal transduction pathway", TIBS 19; Jul. 1994; pp. 279-281.
Caplus 113:106314, Abstract of JP 2022650, Silver halide color photographic material containing a cyan coupler of 2-ureido-phenol type to improve dye developability and remove lecuo cyan dye, Noboru Mizukura et al. Jan. 25, 1990.
Caplus 113:142130, Abstract of JP 2023337, Silver halide photographic material containing phenolic cyan coupler a colorless cyan coupler, Toshiniko Yagi et al., Jan. 25, 1990.
Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat", Chemical Life Science, pp. 157-166, 1977.
Caplus 127:293717, "Optical properties of segmented oligourethane with azomethine terminal fragments", National Academy of Science of Ukraine, M. V. Kurik et al., pp. 2038-2041, 1996.

Caplus 127:273945, "Quantitative structure-biodegradability studies: an investigation of the MITI aromatic compound database", School of Pharmacy and Chemistry, J. C. Dearden, Biodegradability Prediction Edited by Willie J.G.M. Peijnenburg et al., NATO ASI Series, 2, Environment—vol. 23, pp. 93-104, 1996.
Caplus 126:166148, "Inhibitors of coenzyme A-independent transacylase induce apoptosis in human HL-60 cells", James D. Winkler et al., J. Pharmacol. Exp. Ther. pp. 956-966, 1996.
Caplus 98:78152, Abstract of JP 57185219, "Antitumor benzophenone derivatives", Nov. 15, 1982.
Caplus 72:79046, Abstract of CH 479557, "Tuberculostatic and cancerostatic polybasic ureas", Dr. A. Wander, Oct. 15, 1969.
Caplus 125:245169, "Production of murine monoclonal antibodies against sulcofuron and flucofuron by in vitro immunization", G. A. Bonwick et al., J. Immunol. Methods, pp. 163-173, 1996.
Caplus 127:34137f, "Preparation of quinoline an dquinazoline derivatives inhibiting platelet-derived growth factor receptor autophosphorylation", Kazuo Kube et al., May 15, 1997.
Caplus 131:58658k, "Inhibition of raf kinase using symmetrical and unsymmetrical substituted diphenyl ureas", Miller, Scott, Jul. 1, 1999.
Caplus 131:87909y, "Inhibition of p38 kinase activity using substituted heterocyclic ureas", Jacques Dumas, Jul. 1, 1999.
Caplus 131:73649b, "Preparation of pyrazolyl aryl ureas and related compounds as p38kinase inhibitor", Jacques Dumas, Jul. 1, 1999.
Joseph V. Simone, "Cecil Textbook of Medicine", 20th Edition, vol. 1, Feb. 3, 1997. pp. 1004-1010.
Cesar Raposo et al., "Catalysis of Nucleophilic Addition of Pyrrolidine to 2-(5H)-Furanone through Chromenone Cleft-Type Receptors", vol. 37, No. 38, pp. 6947-6950, 1996.
Jacqueline E. van Muijiwijk-Koezen et al., "Isoquinoline and Quinazoline Urea Analogues as Antagonists for the Human Adenosine A$_3$ Receptor", J. Ed. Chem. 2000, 43, pp. 2227-2238, Jan. 3, 2000.
Jacques Dumas et al., "1-Phenyl-5-pyrazolyl Ureas: Potent and Selective p38 Kinase Inhibitors", Bioorganic & Medicinal Chemistry Letters, pp. 2051-2054, May 2, 2000.
Robert W. Carling et al., "1-(3-Cyanobenxylpiperidin-4-yl)-5-methyl-4-phenyl-1,3-dihydroimidazol-2-one: A Selective High-Affinity Antagonist for the Human Dopamine D$_4$ Receptor with Excellent Selectivity over Ion Channels", J. Med. Chem., 1999, 42, pp. 2706-2715.
Abstract WO 9822103, May 28, 1998, John Philip Hedge et al.
Abstract of DE 3305866A1, Aug. 29, 1984, Dr. Acker Rolf-Dieter et al.
Abstract of EP 4931(equivalent 4,240,820), K. Dickore e tal. (1980).
Dumas, J.. "CAS Substructure," May 6, 1997, pp. 1-29.
Scott,Bill, "Substructure (Patent Families)", Aug. 11, 1997, pp. 1-19.
Scott, Bill, "Substructure #2", Nov. 25, 1997, pp. 1-3.
"Beilstein number" Collection, 28 pages (1997).
"Beilstein Collection", 4 pages (1997).
Scott, Bill, "Substructure Search", Dec. 2, 1997, pp. 1-51.
Substructure Search, pp. 1-30. (1997).
Derwent World Patents Index Search, pp. 20-26, (1997).
Abstract of EP 116,932 (1984).
Abstract of EP 676,395 (1995).
Abstract of EP 0 202 538 (1986).
Abstract of EP 16,371 (1980).
A "Notice of References Cited" from the USPTO for U.S. Appl. No. 08/995,749.
A "Notice of References Cited" from the USPTO for U.S. Appl. No. 09/083,399.
A "Notice of References Cited" from the USPTO for U.S. Appl. No. 09/425,228.
A "Notice of References Cited" from the USPTO for U.S. Appl. No. 09/425,229.
A "Notice of References Cited" from the USPTO for U.S. Appl. No. 09/458,015.
A "Notice of References Cited" from the USPTO for U.S. Appl. No. 09/472,232.
A "Notice of References Cited" from the USPTO for U.S. Appl. No. 09/472,232.

A "Notice of References Cited" from the USPTO for U.S. Appl. No. 09/773,604.
A "Notice of References Cited" from the USPTO for U.S. Appl. No. 09/773,659.
A "Notice of References Cited" from the USPTO for U.S. Appl. No. 09/773,672.
A "Notice of References Cited" from the USPTO for U.S. Appl. No. 09/773,675.
A "Notice of References Cited" from the USPTO for U.S. Appl. No. 09/776,935.
A "Notice of References Cited" from the USPTO for U.S. Appl. No. 09/776,936.
A "Notice of References Cited" from the USPTO for U.S. Appl. No. 09/777,920.
A "Notice of References Cited" from the USPTO for U.S. Appl. No. 09/948,915.
A "Notice of References Cited" from the USPTO for U.S. Appl. No. 10/042,226.
A "Notice of References Cited" from the EPO fro European application EP 98/963809.
Supplemental search report from the EPO for European application EP 98/963810.
Supplemental search report from the EPO for European application EP 98/965981.
Supplemental search report from the EPO for European application EP 00/903239.
International search report for International Application No. PCT/US98/10375.
International search report for International Application No. PCT/US98/10376.
International search report for International Application No. PCT/US98/26078.
International search report for International Application No. PCT/US98/26079.
International search report for International Application No. PCT/US98/26080.
International search report for International Application No. PCT/US98/26081.
International search report for International Application No. PCT/US98/26082.
International search report for International Application No. PCT/US98/27265.
International search report for International Application No. PCT/US00/00648.
International search report for International Application No. PCT/US00/00768.
International search report for International Application No. PCT/US02/12064.
International search report for International Application No. PCT/US02/12066.
Co-pending U.S. Appl. No. 09/640,780, filed Aug. 18, 2000.
Co-pending U.S. Appl. No. 09/472,232, filed Dec. 27, 1999.
Co-pending U.S. Appl. No. 09/776,936, filed Dec. 22, 1998.
Co-pending U.S. Appl. No. 09/776,935, filed Dec. 22, 1998.
Co-pending U.S. Appl. No. 09/993,647, filed Nov. 27, 2001.
Co-pending U.S. Appl. No. 10/086,417, filed Mar. 4, 2002.
Co-pending U.S. Appl. No. 10/071,248, filed Feb. 11, 2002.
Co-pending U.S. Appl. No. 10/308,187, filed Dec. 3, 2002.
Co-pending U.S. Appl. No. 10/361,859, filed Feb. 11, 2003.
Internal Medicine, 4$^{th}$ Edition, 1994, pp. 699-715.
Johannes L. Bos, "Ras oncogenes in human cancer: a review," *Cancer Research*, 49, 4682-4689, Sep. 1, 1989.
Kempter et al., "Synthese potentieller Pflanzenschutz- und Schädlingsbekämpfungsmittel aus substituierten Anilinen," Pädagosische Hochschule, Eingegangen am Jan. 7, 1982, 101-120.
Lyons et al., "Discovery of a novel Raf kinase inhibitor," *Endocrine-Related Cancer*, (2001) 8, 219-225.
Lowinger et al., "Design and discovery of small molecules targeting Raf-1 kinase," *Current Pharmaceutical Design*, 2002, 8, 2269-2278.
Dumas et al., "Recent developments in the discovery of protein kinase inhibitors from the urea class," *Current Opinion in Drug Discovery & Development*, 2004, 7(5):600-616.

Dumas, "Protein kinase inhibitors from the urea class," *Current Opinion in Drug Discovery & Development*, 2002, 5(5):718-727.
Lowinger et al., "Discovery of novel class of potent Raf kinase inhibitors: structure activity relationships," *Clinical Cancer Research*, vol. 6, Nov. 2000, 4533s.
Hotte et al., "BAY 43-9006: Early Clinical Data in Patients with Advanced Solid Malignancies," *Current Pharmaceutical Design*, 2002, 8, 2249-2253.
Lee et al., "BAY-43-9006: Bayer/Onyx," *Current Opinion in Investigational Drugs*, 2003, 4(6):757-763.
Sorbara et al., "BAY-43-9006," *Drugs of the Future*, 2002, 27(12):1141-1147.
Khire et al., "Omega-carboxypyridyl substituted ureas as raf kinase inhibitors: SAR of the amid substituent," *Bioorg. Med. Chem. Lett.*, 14 (2004), 783-786.
Wilhelm et al., "BAY 43-9006 Exhibits broad spectrum oral antitumor activity and targets the RAF/MEK/ERK pathway and receptor tyrosine kinases involved in tumor progression and angiogenesis," *Cancer Research*,. 64, 7099-7109, Oct. 1, 2004.
Smith, et al., "Discovery of heterocyclic ureas as a new class of raf kinase inhibitors: identification of a second generation lead by a combinatorial chemistry approach." *Bioorganic & Medicinal Chemistry Letters*, 11 (2001) 2775-2778.
Bankston et al., "A sealeable synthesis of BAY 43-9006: a potent raf kinase inhibitor for the treatment of cancer," *Organic Process Research & Development*, 2002, 6, 777-781.
Caplus 86:72448, Abstract JP 57053785, Pyridine derivatives, Maeda Ryozo et al., Nov. 15, 1982.
Caplus 84:180049, Abstract JP 56029871, Hamada Yoshinori et al., Jul. 10, 1981.
Caplus 84:43857, Abstract JP 58021626, Maeda Ryozo et al., May 2, 1983.
Abstract of JP 55162772, Substituted acetic derivatives, Shionogi & Co., May 23, 1980.
Abstract of EP 0 202 538 A1, "Growth Promoting Agents", Nov. 26, 1986.
Abstract of DE 3305866 A (EP equivalent 116,932), R.D. Acker et al., Aug. 23, 1984.
Abstract of EP 116,932, Aug. 29, 1984.
Abstract of EP 16,371, Oct. 1, 1980.
Abstract of EP 4931A (Equivalent 4,240,820), Dickore, K. et al.
Abstract of EP 0405233A1, Tetsuo Sekiya et al.
Abstract of EP 0 676 395 (U.S. equivalent 5,698,581), Dec. 16, 1997.
Abstract WO 9822103, Hedge May 28, 1998, Philip et al.
Chemical Abstract, vol. 116, No. 21, May 25, 1992, pp. 741-742.
Tarzia, G. et al., Synthesis and anit-inflammatory properties of some pyrrolo(1H,3H) [3,4-d]pyrimidin-2-ones and pyrrolo(1H,6H)[3,4-d]pyrimidin-2-ones, Chemical Abstracts, vol. 91, 1979, p. 594.
White, A. D., et al., "Heterocyclic Ureas; Inhibitors of Acyl-CoA:Cholesterol O-Acyltransferase as Hypochelesterolemic Agents", J. Med. Chem. 1996, 39, pp. 4382-4395.
Co-pending U.S. Appl. No. 10/361,844, filed Feb. 11, 2003.
Co-pending U.S. Appl. No. 10/361,850, filed Feb. 11, 2003.
Co-pending U.S. Appl. No. 10/060,396, filed Feb. 1, 2002.
Co-pending U.S. Appl. No. 09/458,014, filed Dec. 10, 1999.
Co-pending U.S. Appl. No. 10/125,369, filed Apr. 19, 2002.
Co-pending U.S. Appl. No. 09/889,227, filed Jul. 12, 2001.
XP-001145518 # 4956 Potent *Raf* Kinase Inhibitors from the Diphenylurea Class: Structure Activity Relationships, B. Riedl et al., Bayer Corporation.
XP-001145779 "Antitumor Activity of a C-raf Antisense Oligonucleotide in Combination with Standard Chemotherapeutic Agents against Various Human Tumors Transplanted Subcutaneously into Nude Mice", Thomas Geiger et al., vol. 3, 1179-1185, Jul. 1997.
XP-001145481 +2921 Phase I and Pharmacokinetic Study of the Raf Kinase Inhibitor Bay 43-9006 in Patients with Locally Advanced or Metastic Cancer, Dirk Strumberg et al.Bayer AG.
XP-002232130, "A Phase I Trial of H-ras Antisense Oligonucleotide ISIS 2503 Administered as a Continuous Intravenous Infusion in Patients with Advanced Carcinoma", C. Casey Cunningham et al., 2001 American Cancer Society, vol. 92, No. 5, pp. 1265-1271.

XP-002233466, Medline/NLM, NLM8336809—[Intra-arterial ACNU, CDDP chemotherapy for brain metastases from lung cancer: comparison of cases with and without intra-arterial mannitol infusion], Iwadate Y et al.

Nickel et al., "Carboxylic acid analogues of suramin, potential filaricides," *Indian Journal of Chemistry*, vol. 30B, Feb. 1991, p. 182-187.

Duam et al., "The ins and outs of Raf kinases," TIBS 19, Nov. 1994, p. 474-480.

Campbell et al., "Increasing complexity of Ras signaling," *Oncogene*, (1998) 17, 1395-1413.

Bolton et al., "Ras oncogene directed approaches in cancer chemotherapy," *Annual Reports in Medicinal Chemistry*, 29, pp. 165-174.

Moelling et al., "Signal transduction as target of gene therapy," Institute of Medical Virology, University of Zürich, *Recent Results in Cancer Research*, vol. 142, pp. 63-71.

Strumberg et al., "Results of phase I pharmacokinetic and pharmacodynamic studies of the raf kinase inhibitor BAY 43-9006 in patients with solid tumors," *International Journal of Clinical Pharmacology and Therapeutics*, vol. 40, No. 12/2002 (580-581).

Chang et al., "BAY 43-9006 (Sorafenib) inhibitors ectopic (s.c.) and orthotopic growth of a murine model of renal adenocarcinoma (Renca) predominantly through inhibition of tumor angiogenesis," 96th Annual Meeting, Apr. 16-20, 2005, Anaheim/Orange County, CA.

Panka et al., "BAY 43-9006 induces apoptosis in melanoma cell lines," 96th Annual Meeting, Apr. 16-20, 2005, Anaheim/Orange County, CA.

Auclair, et al., "BAY 43-9006 (Sorafenib) is a potent inhibitor of FLT3 tyrosine kinase signaling and proliferation in AML cells," 96th Annual Meeting, Apr. 16-20, 2005, Anaheim/Orange County, CA.

Murphy et al., "BAY 43-9006 controls tumor growth through inhibition of vascular development," 96th Annual Meeting, Apr. 16-20, 2005, Anaheim/Orange County, CA.

Spronsen et al., "Novel treatment strategies in clear-cell metastatic renal cell carcinoma," *Anti-Cancer Drugs*, 2005, 16:709-717.

Thaimattam et al., "3D-QSAR CoMFA, CoMSIA studies on substituted ureas as Raf-1 kinase inhibitors and its confirmation with structure-based studies," *Bioorganic & Medicinal Chemistry*, 12(2004) 6415-6425.

Danson et al., "Improving outcomes in advanced malignant melanoma," *Drugs*, 2005, 65(6):733-743.

Heim et al., "Antitumor effect and potentiation or reduction in cytotoxic drug activity in human colon carcinoma cells by the Raf kinase inhibitor (RKI) BAY 43-9006," *International Journal of Clinical Pharmacology and Therapeutics*, vol. 41, No. 12/2003 (616-617).

Richly et al., "Results of a phase I trial of BAY 43-9006 in combination with doxorubicin in patients with primary hepatic cancer," *International Journal of Clinical Pharmacology and Therapeutics*, vol. 42, No. 11/204 (650-651).

Mross et al., "Drug-drug reaction pharmacokinetic study with the Raf kinase inhibitor (RKI) BAY 43-9006 administered in combination with irinotecan (CPT-11) in patients with solid tumors," *International Journal of Clinical Pharmacology and Therapeutics*, vol. 41, No. 12/2003 (618-619).

Richly et al., "A phase I clinical and pharmacokinetic study of the Raf kinase inhibitor (RKI) BAY 43-9006 administered in combination with doxorubicin in patients with solid tumors," *International Journal of Clinical Pharmacology and Therapeutics*, vol. 41, No. 12/2003 (620-621).

DeGrendele, "Activity of the raf kinase inhibitor BAY 43-9006 in patients with advanced solid tumors," *Clinical Colorectal Cancer*, May 2003, pp. 16-18.

Hubbard, "Oncogenic mutations in B-Raf: some losses yield gains," Skirball Institute of Biomolecular Medicine and Department of Pharmacology, New York University School of Medicine, New York, NY.

Thompson et al., "Recent progress in targeting the Raf/MEK/ERK pathway with inhibitors in cancer drug discovery," *Curr. Opin. Pharmacol.*, Aug. 2005, 5(4):350-6.

Moore et al., "Phase I study to determine the safety and pharmacokinetics of the novel Raf kinase and VEGFR inhibitor BAY 43-9006, administered for 28 days on/7 days off in patients with advanced, refractory solid tumors," *Annals of Oncology*, 16:1688-1694, 2005.

Ahmed et al., "Kinase inhibition with BAY 43-9006 in renal cell carcinoma," *Clinical Cancer Research*, vol. 10, 6388s-6392s, Sep. 15, 2004.

Wan et al., "Mechanism of activation of the RAF-ERK signaling pathway by oncogenic mutations of B-RAF," *Cell*, vol. 116, 855-867, Mar. 19, 2004.

Hanson, "Pulmonary-Allergy, Dermatological, Gastrointestinal & Arthritis, Inhibitors of p38 kinase," *Exp. Opin. Ther. Patents*, (1997) 7(7):729-733.

Strumberg et al., "Phase I clinical and pharmacokinetic study of the novel raf kinase and vascular endothelial growth factor receptor inhibitor BAY 43-9006 in patients with advanced refractory solid tumors," *Journal of Clinical Oncology*, vol. 23, No. 5, Feb. 10, 2005, 965-972.

Regan et al., "Pyrazole urea-based inhibitors of p38 MAP kinase: from lead compound to clinical candidate," *J. Med. Chem.*, 2002, 45, 2994-3008.

Clark et al., "Safety and pharmacokinetics of the dual action raf kinase and vascular endothelial growth factor receptor inhibitor, BAY 43-9006, in patients with advanced, refractory solid tumors," *Clin. Cancer Res.*, 2005:11(15), Aug. 1, 2005, 5472-5480.

Wilson et al., "The structural basis for the specificity of pyridinylimidazole inhibitors of p38 MAP kinase," *Chemistry & Biology*, 1997, vol. 4, No. 6, 423-431.

Hotte et al., "BAY 43-9006: early clinical data in patients with advanced solid malignancies," *Current Pharmaceutical Design*, 2002, 8, 2249-2253.

Jeffcoat et al., "The metabolism and toxicity of halogenated carbanilides," *Drug Metabolism and Deposition*, vol. 5, No. 2, 157-166.

Murata et al., "Facile synthesis of new pyrrolo[3,4-*d*]pyrimidine-2,4-diones," *Chem. Pharm. Bull.*, 22(5) 1212-1213 (1974).

Yasuo et al, "Intra-arterial ACNU, CDDP chemotherapy for brain metastases from lung cancer: comparison of cases with and without intra-arterial mannitol infusion," *Neurol. Surg.*, (1993) vol. 21, No. 6, pp. 513-518.

Murata et al., "Facile synthesis of new pyrrolo[3,4-d]pyrimidine-2,4-diones," *Chemical & Pharmaceutical Bulletin*, (1974), 22(5):1212-13.

Hanson, "Inhibitors of p38 kinase," *Expert Opinion on Therapeutic Patents*, Jul. 1997, vol, 7, No. 7, pp. 729-733(5).

Garcia-Lopez et al., "New routes for the synthesis of pyrrolo[3,2-d]- and [2,3-d]pyrimidine systems starting from a common pyrrole derivative," *Journal of the Chemical Society*, Perkin Transactions 1: Organic and Bio-Organic Chemistry (1972-1999) (1978), (5), 483-7.

Wilhelm et al., "BAY 43-9006: preclinical data," *Curr Pharm Des*, 2002, 8(25):2255-7.

Wright et al., "Clinical trials referral resource. Current clinical trials of BAY 43-9006, Part 1," *Oncology*, Apr. 2005, 19(4):499-502.

Dumas, "Protein kinase inhibitors from the ureas class," *Current Opinion in Drug Discovery & Development*, 2002, vol. 5, No. 5, 718-727.

Patent Abstracts of Japan, Publication No. 02-023337, published Jan. 28, 1990.

Patent Abstracts of Japan, Publication No. 02-022650, published Jan. 25, 1990.

Wisaner at al., "Analogues of platelet activating factor. 7. Bis-aryl amide and bis-aryl urea receptor antagonists of PAF," *J. Med. Chem.*, 1992, 35, 4779-4789.

Ravi et al., "Activated raf-1 causes growth arrest in human small cell lung cancer cells," *J. Clin. Invest.*, pp. 153-159.

Lemoine, "Overview of ras oncogenes and their clinical potential," Chapter 10.

*Drug, facts and comparisons*, 1994 Edition, pp. 2703-2705.

Siu et all, "Phase I study of oral raf-1 kinase inhibitor BAY 43-9006 with gemcitabine in patients with advanced solid tumors," *Proc Am Soc Clinic Oncol*, 22:207, 2003 (abstr 828).

Escudier et al., "Randomized phase III trial of the raf kinase and VEGFR inhibitor sorafenib (BAY 43-9006) in patients with advanced renal cell carcinoma (RCC)," Meeting: *2005 ASCO Annual Meeting*, Category: Genitourinary Cancer, Subcategory: Kidney Cancer, Abstract No. 4510.

Eisen et al., "Phase I trial of BAY 43-9006 (sorafenib) combined with dacarbazine (DTIC) in metastatic melanoma patients," Meeting: *2005 ASCO Annual Meeting*, Category: Melamona, Subcategory: Melamona, Abstract No. 7508.

Adjei et al., "A phase I study of BAY 43-9006 and gefitinib in patients with refractory or recurrent non-small-cell lung cancer (NSCLC)," Meeting: *2005 ASCO Annual Meeting*, Category: Developmental Therapeutics: Molecular Therapeutics, Subcategory: Antiangiogenic or Antimetastatic agents, Abstract No. 4510.

Carling et al., "1-(3-cyanobenzylpiperidin-4-yl)-5-methyl-4-phenyl-1,3-dihydroimidazol-2-one: a selective high-affinity antagonist for the human dopamine $D_4$ receptor with excellent selectivity over ion channels," *J. Med. Chem.*, 1999, 42, 2706-2715.

Van Muijlwijk-Koezen et al., "Isoquinoline and quinazoline urea analogues as antagonists for the human adenosine $A_3$ receptor," *J. Med. Chem.*, 2000, 43, 2227-2238.

Eisenhauer et al., "Impact of new non-cytotoxics in the treatment in ovarian cancer," *Int. J. Gynecol Cancer*, 2001, 11 (Suppl. 1), 68-72.

Kubo et al., "Synthesis and structure-activity relationship of quinazoline-urea derivatives as novel orally active VEGF receptor tyrosine kinase selective inhibitors," #913, XP-001152608.

Carter et al, "Anti-tumor efficacy of the orally active raf kinase inhibitor BAY 43-9006 in human tumor xenograft models," #4954, XP-001145482.

Strumberg et al., "Phase I and pharmacokinetic study of the raf kinase inhibitor bay 43-9006 in patients with locally advanced or metastatic cancer," #2921, XP-001145481.

Dumas et al., "1-phenyl-5-pyrazolyl ureas: potent and selective p38 kinase inhibitors," *Bioorganic & Medicinal Chemistry Letters*, 10 (2000), 2051-2054.

Riedl et al., "Potent raf kinase inhibitors from the diphenylurea class: structure activity relationships," #4956, XP-001145518.

Iwadate et al., "Intra-arterial ACNU, CDDP chemotherapy for brain metastases from lung cancer: comparison of cases with and without intra-arterial mannitol infusion," Dept of Neurological Surgery, Chiba Cancer Center Hospital, Clinical Trial, Journal Article, Randomized Controlled Trial, vol. 21, No. 6, 513-518.

Geiger et al., "Antitumor activity of a C-raf antisense oligonucleotide in combination with standard chemotherapeutic agents against various human tumors transplanted subcutaneously into nude mice," *Clinical Cancer Research*, vol. 3, 1179-1185, Jul. 1997.

Cunningham et al., "A phase I trial of H-ras antisense oligonucleotide ISIS 2503 administered as a continuous intravenous infusion in patients with advanced carcinoma," *Cancer*, Sep. 2001, vol. 92, No. 5, 1265-1271.

PYRIDINE, QUINOLINE, AND ISOQUINOLINE N-OXIDES AS KINASE INHIBITORS

This application is a continuation of U.S. application Ser. No. 10/361,850, filed on Feb. 11, 2003, now abandoned, which claims the benefit of U.S. Provisional Application No. 60/354,935 filed on Feb. 11, 2002.

FIELD OF THE INVENTION

This invention relates to urea compounds containing a pyridine, quinoline, or isoquinoline functionality, which are useful in the treatment of:
(i) raf mediated diseases, for example, cancer,
(ii) p38 mediated diseases such as inflammation and osteoporosis, and
(iii) VEGF mediated diseases such as angiogenesis disorders.

BACKGROUND OF THE INVENTION

Activation of the Ras signal transduction pathway indicates a cascade of events that have a profound impact on cellular proliferation, differentiation, and transformation. Raf kinase, a downstream effector of Ras, is a key mediator of these signals from cell surface receptors to the cell nucleus (Lowy, D. R.; Willumsen, B. M. *Ann. Rev. Biochem.* 1993, 62, 851; Bos, J. L. *Cancer Res.* 1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75). Thus, small molecule inhibitors of Raf kinase activity are important agents for the treatment of cancer (Naumann, U.; Eisenmann-Tappe, I.; Rapp, U. R. *Recent Results Cancer Res.* 1997, 143, 237; Monia, B. P.; Johnston, J. F.; Geiger, T.; Muller, M.; Fabbro, D. *Nature Medicine* 1996, 2, 668).

Inhibition of p38 has been shown to inhibit both cytokine production (eg., TNFα, IL-1, IL-6, IL-8) and proteolytic enzyme production (eg., MMP-1, MMP-3) in vitro and/or in vivo. The mitogen activated protein (MAP) kinase p38 is involved in IL-1 and TNF signaling pathways (Lee, J. C.; Laydon, J. T.; McDonnell, P. C.; Gallagher, T. F.; Kumar, S.; Green, D.; McNulty, D.; Blumenthal, M. J.; Heys, J. R.; Landvatter, S. W.; Stricker, J. E.; McLaughlin, M. M.; Siemens, I. R.; Fisher, S. M.; Livi, G. P.; White, J. R.; Adams, J. L.; Yound, P. R. *Nature* 1994, 372, 739).

Clinical studies have linked TNFα production and/or signaling to a number of diseases including rheumatoid arthritis (Maini. *J. Royal Coll. Physicians London* 1996, 30, 344). In addition, excessive levels of TNFα have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoperosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med.* 1988, 319, 397), endotoxic shock (Beutler et al. *Science* 1985, 229, 869; Ashkenasi et al. *Proc. Nat'l. Acad. Sci. USA,* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995-6, 47, 97) including Crohn's disease (van Deventer et. al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immunol.* 1995, 46, 111), Sarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int,* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taverne et al. *Parasitol. Today* 1996, 12, 290) including *Plasmodium falciparum* malaria Perlmann et al. *Infect. Immunit.* 1997, 65, 116) and cerebral malaria (Rudin et al. *Am J. Pathol.* 1997, 150, 257), non-insulin-dependent diabetes mellitus NDDM; Stephens et al. *J. Biol. Chem.* 1997, 272, 971; Ofei et al. *Diabetes* 1996, 45, 881), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am,* 1987, 67, 69; Marano et al. *Surg. Gynecol. Obstetr.* 1990, 170, 32), multiple sclerosis (M. S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer (MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633).

TNFα levels have also been related to host-versus-graft reactions (Piguet et al. *Immunol. Ser.* 1992, 56, 409) including ischemia reperfusion injury (Colletti et al. *J. Clin. Invest.* 1989, 85, 1333) and allogaft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). TNFα has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma cruzi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdoriferi* (Brandt et al. *Infect. Immunol.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephaloimyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

A number of diseases are thought to be mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim. Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1988, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Bums et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), birth control (Woessner et al. *Steroids* 1989, 54, 491), dystrophobic epidermolysis bullosa (Kronberger et al, *J. Invest. Dermatol.* 1982; 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of TNFα production and MMP production, inhibition of mitogen activated protein (MAP) kinase p38 enzyme provides an approach to the treatment of the above listed diseases including osteoporosis and inflammatory disorders such as rheumatoid arthritis and COPD (Badger, A. M.; Bradbeer, J. N.; Votta, B.; Lee, J. C.; Adams, J. L.; Griswold, D. E. *J. Pharm. Exper. Ther.* 1996, 279, 1453).

Vasculogenesis involves the de novo formation of blood vessels from endothelial cell precursors or angioblasts. The first vascular structures in the embryo are formed by vasculogenesis. Angidgenesis involves the development of capillaries from existing blood vessels, and is the principle mechanism by which organs, such as the brain and the kidney are vascularized. While vasculogenesis is restricted to embryonic development, angiogenesis can occur in the adult, for example during pregnancy, the female cycle, or wound healing.

One major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in lomodimeric forms due to alternative RNA splicing. The VEGF isoforms are highly specific for vascular endothelial cells (for reviews, see: Farrara et al. *Endocr. Rev.* 1992, 13, 18; Neufield et al. *FASEB J.* 1999, 13, 9). VEGF expression is induced by hypoxia (Shweiki et al. *Nature* 1992, 359 843), as well as by a variety of cytokines and growth factors, such as interleukin-1, interleukin-6, epidermal growth factor and transforming growth factor.

To date, VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fins-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. Regulation of the VEGF-mediated signal transduction cascade will therefore provide a useful mode for control of abnormal angiogenesis and/or hyperpermeability processes.

Angiogenesis is regarded as an absolute prerequisite for growth of tumors beyond about 1-2 mm. Oxygen and nutrients may be supplied to cells in tumors smaller than this limit through diffusion. However, every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.*, 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Patho.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 1431, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto-et al. *Lab. Invest.* 1995, 73, 859) and several intracranial tumors (Plate et al. *Nature* 1992, 359, 845; Phillips et al. *Int. J. Oncol.* 1993, 2, 913; Berlanan et al. *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Difer.* 1995, 3, 315).

Overexpression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy; ischemic retinal-vein occlusion, retinopathy of prematurity (Aiello et al. *New Engl. J. Med.* 1994, 331, 1480; Peer et al. *Lab. Invest.* 1995, 72, 638), and age-related macular degeneration (AMD; see, Lopez et al. *Invest. Opththalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels are low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat coltagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

Because inhibition of KDR leads to inhibition of VEGF-mediated angiogenesis and permeabilization, KDR inhibitors will be useful in treatment of diseases characterized by abnormal angiogenesis and/or hyperpermeability processes, including the above listed diseases.

SUMMARY OF THE INVENTION

The current invention provides a kinase inhibitor class of novel diarylureas of formula (I) below, pharmaceutical compositions which contain them and methods for their use. The compounds of the present invention are useful as therapeutic compounds for the treatment and prevention of cancer, inflammation, and osteoporosis.

As inhibitors of raf kinase, these compounds are useful in the treatment of tumors and/or cancerous growth mediated by raf kinase. In particular, the compounds are useful in the treatment of human or animal solid cancers, e.g., murine cancer, carcinomas (e.g., of the lungs, pancreas, thyroid, bladder or colon), myeloid disorders (e.g., myeloid leukemia) or adenomas (e.g., villous colon adenoma).

As inhibitors of p38 mediated events, these compounds are useful in treating cytokine mediated disease states and protease mediated disease states in humans or mammals, wherein the cytokine and protease are those whose production is affected by p38. Accordingly, these compounds are useful therapeutic agents for such acute and chronic inflammatory and/or immunomodulatory diseases as rheumatoid arthritis and osteoporosis.

As inhibitors of VEGF receptor kinases, these compounds are useful in the treatment of diseases where angiogenesis and neovascularization are part of the etiology.

The present invention, therefore, also provides:

(i) methods for the treatment of raf-mediated disease states in humans or mammals, such as cancer, wherein a compound of formula I is administered, or a salt prodrug or isolated stereoisomer thereof, (ii) methods for the treatment of p38-mediated disease states in humans or mammals, such as inflammation, wherein a compound of formula I is administered, or a salt, prodrug or isolated stereoisomer thereof, (iii) methods for the treatment of VEGF-mediated disease states in humans or mammals, such as diabetic retinopathy, wherein a compound of formula I is administered, or a salt, prodrug or isolated stereoisomer thereof.

The invention relates to a compound of formula (I) or a salt, prodrug or isolated stereoisomer thereof (collectively referred to herein as "compounds of this invention"),

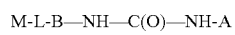

$$M\text{-}L\text{-}B\text{---}NH\text{---}C(O)\text{---}NH\text{-}A \qquad\qquad I$$

wherein A is selected from the group consisting of (i) phenyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $COR^1$, $COOR^1$, $CONR^1R^2$, $NR^1C(O)R^2$, halogen, cyano, and nitro;

(ii) naphthyl, optionally substituted with 1-3 substituents independently selected from the group consisting of $R^1$, $OR^1$, $NR^1R^2$, $S(O)_qR^1$, —$SO_2NR^1R^2$, $NR^1SO_2R^2$, $COR^1$, $COOR^1$, $CONR^1R^2$, $NR^1C(O)R^2$, halogen, cyano, and nitro;

(iii) 5 and 6 membered monocyclic heteroaryl, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $COR^1$, $COOR^1$, $CONR^1R^2$, $NR^1COR^2$, halogen, cyano, and nitro; and (iv) 8-10 membered bicyclic heteroaryl, having 1-6 heteroatoms independently selected from the group consisting of O, N and S, optionally substituted with 1-3 substituents independently selected from the group consisting of R, $OR^1$, $NR^1R^2$, $S(O)_qR^1$, $SO_2NR^1R^2$, $NR^1SO_2R^2$, $COR^1$, $COOR^1$, $CONR^1R^2$, $NR^1COR^2$, halogen, cyano, and nitro.

B is selected from the group consisting of (i) phenylene, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro;

(ii) naphthylene, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro;

(iii) 5 and 6 membered monocyclic heteroaryl-ene, having 1-3 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro; and (iv) 8-10 membered bicyclic heteroaryl--ene, having 1-6 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro.

L is selected from the group consisting of:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^{3a}$—$(CH_2)_l$—,
(e) —$(CH_2)_m$—$NR^{3a}$(O)—$(CH_2)_l$—,
(f) —$(CH_2)_m$—S—$(CH_2)_l$—,
(g) —$(CH_2)_m$—C(O)$NR^{3a}$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—, and
(k) —$(CH_2)_m$—$CR^{3a}$(OH)—$(CH_2)_l$—;
(l) —$(CH_2)_m$—C≡C—$(CH_2)_l$—;
(m) —$(CH_2)_m$—C=C—$(CH_2)_l$—;
(n) a single bond; and
(o) —$(CH_2)_m$—$CR^{3a}R^{3b}$$(CH_2)_l$—;

wherein m and l are integers independently selected from 0-4.

M is selected from the group consisting of
a) pyridine-1-oxide substituted 1 to 3 times by a substituent selected from the group consisting of —C(O)$NR^4R^5$, —C($NR^4$)$R^5$, —C(O)$R^4$, —$SO_2R^4$, and —$SO_2NR^4R^5$; which is optionally additionally substituted by $Z_r$;

b) quinoline-1-oxide, which is optionally substituted by $Z_n$; and c) isoquinoline-1-oxide, which is optionally substituted by $Z_n$;

wherein
r is 0-2,
n is 0-3, and
each Z is independently selected from the group consisting of $R^4$, halogen, cyano, —$CO_2R^4$, —C(O)$R^4$, —C(O)$NR^4R^5$, —$NO_2$, —$OR^4$—, —$NR^4R^5$, —$NR^4$C(O)$OR^5$, —$NR^4$C(O)$R^5$, —S(O)$_p$$R^4$, and —$SO_2NR^4R^5$.

Each $R^1$, $R^2$, $R^4$ and $R^5$ are independently selected from the group consisting of:
(a) hydrogen,
(b) $C_1$-$C_5$ linear, branched, or cyclic alkyl,
(c) phenyl,
(d) 5-6 membered monocyclic heteroaryl heteroaryl having 1-4 heteroatoms selected from the group consisting of O, N and S or 8-10 membered bicyclic heteroaryl having 1-6 heteroatoms selected from the group consisting of O, N and S,
(e) $C_1$-$C_3$ alkyl-phenyl,
(f) $C_1$-$C_3$ alkyl heteroaryl having 1-4 heteroatoms selected from the group consisting of O, N and S, said heteroaryl including 5-6 membered monocyclic and 8-10 membered bicyclic heteroaryl, and
(g) up to per-halo substituted $C_1$-$C_5$ linear or branched alkyl. $R^{3a}$ and $R^{3b}$ are independently, hydrogen or $C_1$-$C_5$ linear or branched alkyl.

Each $R^1$, $R^2$, $R^4$ and $R^5$, when not hydrogen or perhalo substituted $C_1$-$C_5$ linear or branched alkyl, are optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, amino, $C_1$-$C_3$ alkylamino, $C_1$-$C_6$ dialkylamino, halogen, cyano, and nitro;
and p and q are integers each independently selected from 0, 1, or 2.

The compounds of this invention do not include compounds of Formula II below, or salts, prodrugs or isolated stereoisomers thereof,

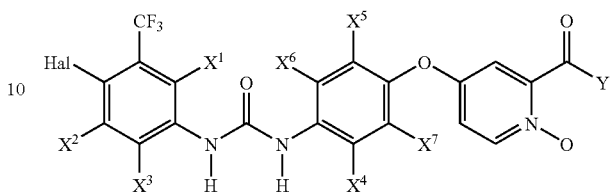

II wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$X^1$ to $X^7$ are each, independently, H, OH or O(CO)$C_1$-$C_4$ alkyl.

For compounds of formula II, the C(O)Y substituted pyridine-1-oxide conforms to M of formula I, the $X^4$ to $X^7$ substituted phenyl conforms to B of formula I, the oxygen bridge, —O—, conforms to L of formula I and the $X^1$ to $X^3$ substituted 3-trifluoromethyl-4-halo-phenyl conforms to A of formula I.

It is understood that the term "pyridine-1-oxide" used throughout this document includes those structures referred to in the art as 1-oxo-pyridine and 1-hydroxy-pyridine. For example, ChemInnovation Software, Inc. Nomenclator™ v. 3.01 identifies compounds of formula II where Y=$NHCH_3$, Hal=Cl and $X^1$-$X^7$=H, drawn in ChemDraw, as N-[4-chloro-3-(trifluoromethylphenyl]({4-[1-hydroxy-2-(N-methylcarbamoyl)(4-pyridyloxy)]phenyl}amino)carboxamide. The same remark applies to the quinoline-1-oxides and the isoquinoline-1-oxides.

Suitable substituted and unsubstituted heteroaryl groups for the compounds of this invention, such as those for A and B of formula I, include, but are not limited to monocyclic heteroaryl groups such as 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 3- or 4-pyridazinyl and 2-,3-pyrazinyl.

Suitable substituted and unsubstituted heteroaryl groups for the compounds of this invention, such as those for A and B of formula I, include, but are not limited to bicyclic heteroaryl groups. Examples of bicyclic heteroaryl rings include 5-5, 5-6, and 6-6 fused bicycles, where one of the rings is one of the above heteroaryl rings and the second ring is either benzene or another heteroaryl ring, for example 2-, 3-, 4-, 5-, 6- or 7-benzofuryl, 2-, 3-, 4-, 5-, 6-or 7-benzothienyl, 1-, 2-, 3-, 4-, 5-, 6- or 7-indazolyl, 1-, 2-, 3-, 4-, 5-, 6-, or 7-isoindolyl, 1-, 2-, 4- or 5-benzimidazolyl, 1-, 3-, 4-; 5-, 6- or 7-indazolyl (benzopyrazolyl), 2-, 4-, 5-, 6- or 7-benzoxazolyl, 3-, 4-, 5- 6- or 7-benzisoxazolyl, 1-, 3-, 4-, 5-, 6- or 7-benzothiazolyl, 2-, 4-, 5-, 6- or 7-benzothiazolyl, 2-, 4-, 5-, 6-, or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, or 2-, 4-, 5-, 6-, 7- or 8-quinazolinyl.

More specifically, the substituted heteroaryl groups can be, for example, 5-methyl-2-thienyl, 4-methyl-2-thienyl, 1-methyl-3-pyrryl, 1-methyl-3-pyrazolyl, 5-methyl-2-thiazolyl, 5-methyl-1,2,4-thiadiazol-2-yl and others.

Suitable linear alkyl groups and alkyl portions of groups, e.g., alkoxy, alkylphenyl and alkylheteroaryl etc. throughout include methyl, ethyl, propyl, butyl, pentyl, etc. Suitable branched alkyl groups include all branched isomers such as isopropyl, isobutyl, sec-butyl, tert-butyl, etc.

The term "up to perhalo substituted linear and branched alkyl," includes alkyl groups having one alkyl hydrogen replaced with halogen, alkyl groups wherein all hydrogens are replaced with halogen, alkyl groups wherein more than one but less than all hydrogens are replaced by halogen and alkyl groups having alkyl hydrogens replaced by halogen and other substituents.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety. Preferred halogens are Cl, Br and F.

The term "cycloalkyl", as used herein, refers to cyclic structures having 3-8 members in the ring such as cyclopropyl, cyclobutyl and cyclopentyl and cyclic structures having 3-8 members with alkyl substituents such that, for example, "$C_3$ cycloalkyl" includes methyl substituted cyclopropyl groups.

The term "saturated carbocyclic moieties" defines only the cyclic structure, i.e. cyclopentyl, cyclohexyl, etc. Any alkyl substitution on these cyclic structures is specifically identified.

Particularly preferred compounds of this invention are defined by formula I, wherein:

A is selected from phenyl, naphthyl, furyl, isoindolyl, oxadiazolyl, oxazolyl, isooxazolyl, indolyl, indazolyl, benzothiazolyl, benzimidazolyl, benzoxazolyl, pyrazolyl, pyridinyl, pyrimidinyl, pyrrolyl, quinolinyl, isoquinolinyl, tetrazolyl, thiadiazolyl, thiazolyl and thienyl, B is selected from phenylene, naphthylene, thienylene, furylene, pyridine-ene, quinoline-ene, isoquinoline-ene, indole-ene, L is selected from —CH$_2$O—, —OCH$_2$—, —O—, a single bond, —CH$_2$—, —NH—, —N(CH$_3$)—, —N(CH$_3$)CH$_2$—, —NC$_2$H$_4$—, —C(O)—, —NHCH$_2$—, —N(CH$_3$)C(O)—, —NHC(O)—, —CH$_2$N(CH$_3$)—, —C(O)NH—, —CH$_2$S—, —SCH$_2$—, —S—, —C(O)NCH$_3$—, —CH$_2$C(O)N(CH$_3$)—, —C(O)N(CH$_3$)CH$_2$—, —CF$_2$—, —CCl$_2$—, —CHF— and —CH(OH)—, and M is defined as above.

Particularly preferred substituents for B include methyl, trifluoromethyl, ethyl, n-propyl, n-butyl, n-pentyl, isopropyl, tert-butyl, sec-butyl, methylethyl, methylpropyl, cyclopropyl, cyclobutyl, cyclopentyl, methoxy, ethoxy, propoxy, Cl, Br and F, cyano, nitro, hydroxy, amino, methylamino, dimethylamino, ethylamino and diethylamino, Preferred substituents for A include methyl, trifluoromethyl, ethyl, n-propyl, n-butyl, n-pentyl, i-propyl, t-butyl, methylethyl, methylpropyl, cyclopropyl, cyclobutyl, cyclopentyl, methoxy, methyl sulfonyl, ethoxy, propoxy, butyoxy, pentoxy, phenoxy, pyridyloxy, Cl, Br, F, cyano, nitro, hydroxy, amino, methylamino, dimethylamino, ethylamino and diethylamino. Preferred substituents for A further include substituted or unsubstituted phenyl, pyridyl, pyrimidinyl, quinolinyl, isoquinolinyl, isoindolyl, pyrazolyl, pyridazinyl, pyrrolyl, imidazolyl, indazolyl, thienyl, furyl, isoxazolyl, isothiazolyl, benzothiazolyl, benzyl, and pyridylmethyl.

Preferred substituents for A also include:
NH(C$_1$-C$_5$ alkyl-phenyl or pyridinyl), such as aminophenyl;
N(C$_1$-C$_5$ alkyl)(C$_1$-C$_5$ alkyl, phenyl or pyridinyl), such as diethylamino and dimethyl amino;
S(O)$_2$(C$_1$-C$_5$ alkyl); such as methylsulfonyl;
SO$_2$NH(C$_1$-C$_5$ alkyl);
SO$_2$N(C$_1$-C$_5$ alkyl)(C$_1$-C$_5$ alkyl);
NHSO$_2$(C$_1$-C$_5$ alkyl);
N(C$_1$-C$_3$ alkyl) SO$_2$(C$_1$-C$_5$ alkyl);
CO(C$_1$-C$_6$ alkyl, phenyl or pyridinyl);
COO(C$_1$-C$_6$ alkyl, phenyl or pyridinyl), such as C(O)OCH$_3$, —C(O)OCH$_2$CH$_3$, —C(O)OCH$_2$CH$_2$CH$_3$;
COOH;
CONH$_2$(carbamoyl);
CONH(C$_1$-C$_6$ alkyl, phenyl or pyridinyl), such as N-methylethyl carbamoyl, N-methyl carbamoyl, N-ethylcarbamoyl, N-dimethylamino ethyl carbamoyl;
CON(C$_1$-C$_6$ alkyl, phenyl or pyridinyl)(C$_1$-C$_6$ alkyl, phenyl or pyridinyl), such as N-dimethyl carbamoyl;
NHCO(C$_1$-C$_5$ alkyl, phenyl or pyridinyl) and
N(C$_1$-C$_5$ alkyl)CO(C$_1$-C$_5$ alkyl); each of the above substituents are optionally partially or fully halogenated, such as difluoromethyl sulfonyl and trifluoromethyl sulfonyl An embodiment of this invention includes compounds of this invention wherein in formula I, A, and B are one of the following combinations and M is as defined above:

A=phenyl, B=phenylene,
A=phenyl, B=pyridinyl-ene,
A=phenyl, B=naphthylene,
A=phenyl, B=quinolinyl-ene,
A=phenyl, B=isoquinolinyl-ene,
A=pyridinyl, B=phenylene,
A=pyridinyl, B=pyridinyl-ene,
A=pyridinyl, B=naphthylene,
A=pyridinyl, B=quinolinyl-ene,
A=pyridinyl, B=isoquinolinyl-ene,
A=naphthyl, B=phenylene,
A=naphthyl, B=pyridinyl-ene,
A=naphthyl, B=naphthylene,
A=naphthyl, B=quinolinyl-ene,
A=naphthyl, B=isoquinolinyl-ene,
A=isoquinolinyl, B=phenylene,
A=isoquinolinyl, B=pyridinyl-ene,
A=isoquinolinyl, B=naphthylene,
A=isoquinolinyl, B=quinolinyl-ene
A=isoquinolinyl, B=isoquinolinyl-ene,
A=quinolinyl, B=phenylene,
A=quinolinyl, B=pyridinyl-ene,
A=quinolinyl, B=naphthylene,
A=quinolinyl, B=quinolinyl-ene
A=quinolinyl, B=isoquinolinyl-ene,
A=pyrazolyl, B=phenylene,
A=pyrazolyl, B=pyridinyl-ene,
A=pyrazolyl, B=naphthylene,
A=pyrazolyl, B=quinolinyl-ene,
A=pyrazolyl, B=isoquinolinyl-ene,
A=isoxazolyl, B=phenylene,
A=isoxazolyl, B=pyridinyl-ene,
A=isoxazolyl, B=naphthylene,
A=isoxazolyl, B=quinolinyl-ene;
A=isoxazolyl, B=isoquinolinyl-ene.
A=indazolyl, B=phenylene, A=indazolyl, B=pyridinyl-ene,
A=indazolyl, B=naphthylene,
A=indazolyl; B=quinolinyl-ene and
A=indazolyl, B=isoquinolinyl-ene.

The invention further relates to processes and methods of preparing the novel compounds of this invention.

The invention further relates to pharmaceutical compositions comprising one or more compounds of this invention, or a purified stereoisomet, a pharmaceutically acceptable salt, or a prodrug of a compound of formula (I). The invention also relates to compounds per se, of formula I.

One of ordinary skill in the art will recognize that some of the compounds of Formula (I) can exist in different geometrical isomeric forms. A number of the compounds of Formula I possess asymmetric carbons and can therefore exist in racemic and optically active forms as well as in the form of racemic or nonracemic mixtures thereof, and in the form of diastereomers and diastereomeric mixtures. All of these compounds, including cis isomers, trans isomers, diastereomic mixtures, racemates, nonracemic mixtures of enantiomiers, substantially pure, and pure enantiomers, are considered to be within the scope of the present invention and are collectively referred to when reference is made to compounds of this invention.

Methods of separation of enantiomeric and diastereomeric mixtures are well known to one skilled in the art. The optical isomers can be obtained by resolution of the racemic mixtures according to conventional processes, for example, by the formation of diastereoisomeric salts using an optically active acid or base. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical chemical differences by methods known to those skilled in the art, for example, by chromatography or fractional crystallization. The optically active bases or acids are liberated from the separated diastereomeric salts. A different process for separation of optical isomers involves the use of a chiral chromatography column (e.g., chiral HPLC columns) optimally chosen to maximize the separation of the enantiomers. Suitable chiral HPLC columns are manufactured by Diacel, e.g., Chiracel OD and Chiracel OJ. The optically active compounds of Formula (I) can likewise be obtained by utilizing optically active starting materials. The present invention encompasses any isolated racemic or optically active form of compounds described in Formula I which possess rat p38, and/or VEGFR inhibitory activity. The term stereoisomer is understood to encompass diastereoisomets, enantiomers, geometric isomers, etc. Herein, substantially pure enantiomers is intended to mean that no more than 5% w/w of the corresponding opposite enantiomer is present.

Pharmaceutically acceptable salts of these compounds as well as commonly used prodrugs of these compounds are also within the scope of the invention.

Salts of this invention are especially the pharmaceutically acceptable salts of compounds of formula (I) such as, for example, organic or inorganic acid addition salts of compounds of formula (I). Suitable inorganic acids include but are not limited to halogen acids (such as hydrochloric acid and hydrobromic acid), sulfuric acid, or phosphoric acid. Suitable organic acids include but are not limited to carboxylic, phosphonic, sulfonic, or sulfamic acids, with examples including acetic acid, propionic acid, octanoic acid, decanoic acid, tri-fluoroacetic acid, dodecanoic acid, glycolic acid, lactic acid, 2- or 3-hydroxybutyric acid, γ-aminobutyric acid (GABA), gluconic acid, glucosemonocarboxylic acid, benzoic acid, salicylic acid, phenylacetic acid and mandelic acid, fumaric acid, succinic acid, adipic acid, pimelic acid, suberic acid, azeiaic acid, malic acid, tartaric acid, citric acid, glucaric acid, galactaric acid, amino acids (such as glutamic acid, aspartic acid, N-methylglycine, acetytaminoacetic acid, N-acetylasparagine or N-acetylcysteine), pyruvic acid, acetoacetic acid, methanesulfonic acid, tri-fluoromethane sulfonic acid, 4-toluene sulfonic acid, benzenesulfonic acid, 1-naphthalenesulfonic acid, 2-naphthalenesulfonic acid, phosphoserine, and 2- or 3-glycerophosphoric acid.

In addition, pharmaceutically acceptable salts include acid salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

The formation of prodrugs is well known in the art in order to enhance the properties of the parent compound; such properties include solubility, absorption, biostability and release time (see "*Pharmaceutical Dosage Form and Drug Delivery Systems*" (Sixth Edition), edited by Ansel et al., published by Williams & Wilkins, pages 27-29, (1995) which is hereby incorporated by reference). Commonly used prodrugs of the disclosed oxazolyl-phenyl-2,4-diamino-pyrimidine compounds are designed to take advantage of the major drug biotransformation reactions and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see *Goodman and Gilman's The Pharmacological Basis of Therapeutics* (Ninth Edition), editor Molinoffet al., publ. by McGraw-Hill, pages 11-13, (1996), which is hereby incorporated by reference).

The invention also relates to methods for treating and preventing diseases, for example, hyper-proliferative, inflammatory and angiogenesis disorder and osteoporosis in mammals by administering a compound of this invention or a pharmaceutical composition comprising one or more compounds of this invention.

An embodiment of the present invention is a method for treating diseases in humans and/or other mammals which are mediated by the VEGF induced signal transduction pathway which comprises administering a compound of this invention to a human or other mammal.

Another embodiment of this invention is a method for treating diseases in humans and/or other mammals which are characterized by abnormal angiogenesis or hyperpermeability processes with a compound of this invention to a human or other mammal.

A compound according to the invention can be administered simultaneously with another angiogenesis inhibiting agent to a patient with such a disorder, in the same formulation or, more typically in separate formulations and, often, using different administration routes. Administration can also be sequentially, in any order.

A compound according to the invention can be administered in tandem with another angiogenesis inhibiting agent, wherein a compound according to the invention can be administered to a patient once or more per day for up to 28 consecutive days with the concurrent or intermittent administration of another angiogenesis inhibiting agent over the same total time period The invention also relates to a method of treating or preventing cancer and other hyperproliferative disorders by administering a compound of this invention or a pharmaceutical composition comprising one or more compounds of this invention, optionally in combination with a cytotoxic agent.

Optional anti-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Additional cytotoxic agents include oxaliplatin, gemcitabone, gefinitib, taxotere, ara A, ara C, herceptin, BCNU, CCNU, DTIC, and actinomycin D. Other anti-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, tenipdside, testosterone propionate, thiotepa, trimethylmelamine, uridine, and vinorelbine.

Other anti-proliferative agents suitable for use with the composition of the invention include but are not limited to other anti-cancer agents such as epothilone, irinotecan, raloxifen and topotecan.

The invention also relates to a pharmaceutical preparation which comprises (1) quantities of (a) a compound according to the invention (b) at least one other cytotoxic or cytostatic agent in amounts which are jointly effective for treating a cancer, where any component (a) or (b) can also be present in the form of a pharmaceutically acceptable salt if at least one salt-forming group is present, with (2) one or more pharmaceutically acceptable carrier molecules.

The present invention provides methods for treating a cancer in a mammal, especially a human patient comprising administering an a compound according to the invention optionally in combination with a cytotoxic or cytostatic chemotherapeutic agent including, but not limited to, DNA topoisomerase I and II inhibitors, DNA intercalators, alkylating agents, microtubule disruptors, hormone and growth factor receptor agonists or antagonists, other kinase inhibitors and antimetabolites. The methods of the present invention can be used to treat a variety of mammal hyperproliferative disorders as defined in this specification. The compound according to the invention and the cytotoxic or cytostatic agent are administered to a mammal in quantities which together are therapeutically effective against proliferative diseases. Thus, the compound according to the invention is effective for raf kinase-mediated cancers. However, these compounds are also effective for cancers not mediated by raf kinase.

A compound according to the invention can be administered simultaneously with a cytotoxic or cytostatic agent to a patient with a cancer, in the same formulation or, more typically in separate formulations and, often, using different administration routes. Administration can also be sequentially, in any order.

A compound according to the invention can be administered in tandem with the cytotoxic or cytostatic agent, wherein a compound according to the invention can be administered to a patient once or more per day for up to 28 consecutive days with the concurrent or intermittent administration of a cytotoxic or cytostatic agent over the same total time period.

A compound according to the invention can be administered to a patient at an oral, intravenous, intramuscular, subcutaneous, or parenteral dosage which can range from about 0.1 to about 200 mg/kg of total body weight and the cytotoxic or cytostatic agent can be administered to a patient at an intravenous, intramuscular, subcutaneous, or parenteral dosage which can range from about 0.1 mg to 200 mg/kg of patient body weight.

This invention further relates to kits comprising separate doses of the two mentioned chemotherapeutic agents in separate containers. The combinations of the invention can also be formed in vivo, e.g., in a patient's body.

The term "cytotoxic" refers to an agent which can be administered to kill or eliminate a cancer cell. The term "cytostatic" refers to an agent which can be administered to restrain tumor proliferation rather than induce a cytoreduction yielding the elimination of the cancer cell from the total viable cell population of the patient. The chemotherapeutic agents described herein, e.g., irinotecan, vinorelbine, gemcitabine, and paclitaxel are considered cytotoxic agents. These cytotoxic and cytostatic agents have gained wide spread use as chemotherapeutics in the treatment of various cancer types and are well known in the art. These and other cytotoxic/cytostatic agents can be administered in the conventional formulations and regimens in which they are known for use alone.

Description of Treatment of Hyperproliferative Disorders

Cancer and hyperproliferative disorders are defined as follows. These disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in man, but also exist with a similar etiology in other mammals, and can be treated by pharmaceutical compositions of the present invention.

Conditions within a human or other mammal which can be treated by administering a compound of this invention include tumor growth, retinopathy, including diabetic retinopathy, ischemic retinal-vein occlusion, retinopathy of prematurity and age related macular degeneration; psoriasis, or bullous disorder associated with subepidermal blister formation, including bullous pemphigoid, erythema multiforme, or dermatitis herpetiformis, rheumatoid arthritis, osteoarthritis, septic arthritis, tumor metastasis, periodontal disease, cornal ulceration, proteinuria, coronary thrombosis from atherosclerotic plaque, aneurismal aortic, birth control, dystrophobic epidermolysis bullosa, degenerative cartilage loss following traumatic joint injury, osteopenias mediated by MMP activity, tempero mandibular joint disease or demyelating disease of the nervous system.

Methods of interest treat combinations of conditions such as rheumatic fever, bone resorption, postmenopausal osteoperosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (*Plasmodium falciparum* malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple sclerosis), advanced cancer, lymphoid malignancy, pancreatitis, impaired wound healing in infection, inflammation and cancer, myelodysplastic syndromes, systemic lupus eryhematosus, biliary cirrhosis, bowel necrosis, psoriasis, radiation injury/toxicity following administration of monoclonal antibodies, host-versus-graft reaction (ischemia reperfusion injury and allograft rejections of kidney, liver, heart, and skin), lung allograft rejection (obliterative bronchitis) or complications due to total hip replacement.

Also provided is a method for treating an infectious disease selected from the group consisting of tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum,* cytomegalovirus, influenza virus, Theiler's encephalornyelitis virus, and the human immunodeficiency virus (HIV).

General Preparative Methods

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of this invention can be made according to conventional chemical methods, and/or as disclosed below, from starting materials which are either commercially available or producible according to routine, conventional chemical methods. General methods for the preparation of the compounds are given below, and the preparation of related compounds, is specifically illustrated in Examples.

Ureas of formula (I) can be prepared by a variety of simple methods known in the art. General approaches for the formation of those compounds can be found in "*Advanced Organic Chemistry*", by J. March, John Wiley and Sons, 1985 and in "Comprehensive Organic Transformations", by R. C. Larock, *VCH Publishers,* 1989), which are hereby incorporated by reference.

More specifically, pyridine-1-oxides, quinoline-1-oxides and isoquinoline-1-oxides and their derivatives can be prepared from the corresponding pyridines, quinolines, and isoquinolines using oxidation conditions know in the art. Some examples are as follows:

peracids such as meta chloroperbenzoic acids in chlorinated solvents such as dichloromethane, dichloroethane, or chloroform (Markgraf et al., *Tetrahedron* 1991, 47, 183).

(Me₃SiO)₂ in the presence of a catalytic amount of perrhenic acid in chlorinated solvents such as dichloromethane (Coperet et al., *Terahedron Lett.* 1998, 39, 761)

Perfluoro-cis-2-butyl-3-propyloxaziridine in several combinations of halogenated solvents (Amone et al., *Tetrahedron* 1998, 54, 7831).

Hypofluoric acid—acetonitrile complex in chloroform (Dayan et al., *Synthesis* 1999, 1427).

Oxone, in the presence of a base such as KOH, in water (Robker et al. *J. Chem. Res., Synop.* 1993, 10, 412).

Magnesium monoperoxyphthalate, in the presence of glacial acetic acid (Klemm et al., *J. Heterocylic Chem.* 1990, 6, 1537).

Hydrogen peroxide, in the presence of water and acetic acid (Lin A. J., *Org. Prep. Proced. Int.* 1991, 23(1), 114).

Dimethyldioxirane in acetone (Boyd et al., *J. Chem. Soc., Perkin Trans.* 1991, 9, 2189).

The starting materials for the above mentioned oxidation are bis aryl ureas, which contain either a pyridine, quinoline, or isoquinoline in one of their side chains. Specific preparations of these ureas are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. App., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698.

The following copending U.S. applications are directed to diaryl ureas that find use in the treatment of raf and/or p38 mediated diseases and describe the preparation of specific diaryl ureas that are precursors to the compounds of this invention.

Ser. No. 08/863,022, filed May 23, 1997;
Ser. No. 08/996,344, filed Dec. 22, 1997;
Ser. No. 08/996,343, filed Dec. 22, 1997;
Ser. No. 08/996,181, filed Dec. 22, 1997;
Ser. No. 08/995,749, filed Dec. 22, 1997;
Ser. No. 08/995,750, filed Dec. 22, 1997;
Ser. No. 08/995,751, filed Dec. 22, 1997;
Ser. No. 09/083,399, filed May 22, 1998;
Ser. No. 09/425,228, filed Oct. 22, 1999;
Ser. No. 09/777,920, filed Feb. 7, 2001.
Ser. No. 09/838,285, filed Apr. 20, 2001;
Ser. No. 09/838,286, filed Apr. 20, 2001;

These applications are incorporated herein by reference.

The following published PCT applications are directed to diaryl ureas that find use in the treatment of p38 mediated diseases and also describe the preparation of specific diaryl ureas that are precursors to the compounds of this invention.

WO 99/23091;
WO 00/43384;
WO 00/55152;
WO 00/55139 and
WO 01/36403.

These applications are also incorporated herein by reference.

The invention also includes pharmaceutical compositions including a compound of this invention, and a physiologically acceptable carrier.

The compounds may be administered orally, topically, parenterally, by inhalation or spray or rectally in dosage unit formulations. The term 'administration by injection' includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For all regimens of use disclosed herein for compounds of Formula I, the daily oral dosage regimen will preferably be from 0.01 to 200 mg/kg of total body weight. The daily dosage for administration by injection, including intravenous, intramuscular, subcutaneous and parenteral injections, and use of infusion techniques will preferably be from 0.01 to 200 mg/kg of total body weight. The daily rectal dosage regime will preferably be from 0.01 to 200 mg/kg of total body weight. The daily topical dosage regime will preferably be from 0.1 to 200 mg administered between one to four times daily. The daily inhalation dosage regime will preferably be from 0.01 to 10 mg/kg of total body weight. These dosages can be achieved with multiple dosages within a day or extended dosages (weekly/monthly).

It will be appreciated by those skilled in the art that the particular method of administration will depend on a variety of factors, all of which are considered routinely when administering therapeutics. It will also be appreciated by one skilled in the art that the specific dose level for a given patient depends on a variety of factors, including specific activity of the compound administered, age, body weight, health, sex, diet, time and route of administration, rate of excretion, etc. It will be further appreciated by one skilled in the art that the optimal course of treatment, i.e., the mode of treatment and the daily number of doses of a compound of this invention given for a defined number of days, can be ascertained by those skilled in the art using conventional treatment tests.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the condition undergoing therapy.

The compounds can be produced from known compounds (or from starting materials which, in turn, can be produced from, known compounds), e.g., through the general preparative methods shown below. The activity of a given compound to inhibit raf kinase can be routinely assayed, e.g., according to procedures disclosed below.

The entire enclosure of all applications, patents and publications cited above and below are hereby incorporated by reference, including non-provisional application Ser. No. 09/425,228 filed Oct. 22, 1999, Ser. No. 09/722,418 filed Nov. 28, 2000 and Ser. No. 60/334,609, filed Dec. 3, 2001.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

EXAMPLES

All reactions are performed in flame-dried or oven-dried glassware under a positive pressure of dry argon or dry nitrogen, and are stirred magnetically unless otherwise indicated. Sensitive liquids and solutions are transferred via syringe or cannula, and introduced into reaction vessels through rubber septa. Unless otherwise stated, the term 'concentration under reduced pressure' refers to use of a Buchi rotary evaporator at approximately 15 mmHg. Unless otherwise stated, the term 'under high vacuum' refers to a vacuum of 0.4-1.0 mmHg.

All temperatures are reported uncorrected in degrees Celsius (° C.). Unless otherwise indicated, all parts and percentages are by weight. Commercial grade reagents and solvents are used without further purification.

Thin-layer chromatography (TLC) is performed using Whatman® pre-coated glass-backed silica gel 60A F-254 250 µm plates. Visualization of plates is effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) is performed using 230-400 mesh EM Science® silica gel.

Melting points (mp) are determined using a Thomas-Hoover melting point apparatus or a Mettler FP66 automated melting point apparatus and are uncorrected. Fourier transform infrared spectra are obtained using a Mattson 4020 Galaxy Series spectrophotometer. Proton ($^1$H) nuclear magnetic resonance (NMR) are measured with a General Electric SN-Omega 300 (300 MHz) spectrometer with either Me$_4$Si (δ 0.00) or residual protonated solvent (CHCl$_3$ δ 7.26; MeOH δ 3.30; DMSO δ 2.49) as standard. Carbon ($^{13}$C) NMR spectra are measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) are either obtained as electron impact (EI) mass spectra or as fast atom bombardment (FAB) mass spectra. Electron impact mass spectra (EI-MS) are obtained with a Hewlett Packard 5989A mass spectrometer equipped with a Vacumetrics Desorption Chemical Ionization Probe for sample introduction. The ion source is maintained at 250° C. Electron impact ionization is performed with electron energy of 70 eV and a trap current of 300 μA. Liquid-cesium secondary ion mass spectra (FAB-MS), an updated version of fast atom bombardment is obtained using a Kratos Concept 1-H spectrometer. Chemical ionization mass spectra (CI-MS) are obtained using a Hewlett Packard MS-Engine (5989A) with methane or ammonia as the reagent gas ($1\times10^4$ torr to $2.5\times10^4$ torr). The direct insertion desorption chemical ionization (DCI) probe (Vaccumetrics, Inc.) is ramped from 0-1.5 amps in 10 sec and held at 10 amps until all traces of the sample disappeared (~1-2 min). Spectra are scanned from 50-800 amu at 2 sec per scan. HPLC—electrospray mass spectra (HPLC ES-MS) are obtained using a Hewlett-Packard 1100 HPLC equipped with a quaternary pump, a variable wavelength detector, a C-18 column, and a Finnigan LCQ ion trap mass spectrometer with electrospray ionization. Spectra are scanned from 120-800 amu using a variable ion time according to the number of ions in the source. Gas chromatography—ion selective mass spectra (GC-MS) is obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV). Elemental analyses are conducted by Robertson Microlit Labs, Madison N.J.

Experimental Synthesis 1

N-[4-chloro-3-(trifluoromethyl)phenyl]-N'-{4-[2-(N-methylcarbamoyl)-1-oxo-(4-pyridyloxy)]phenyl} urea

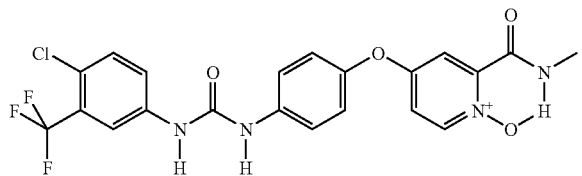

The title compound is not a compound of this invention, and has been distinguished from the compounds of this invention by a proviso. However, its preparation illustrates how other compounds of the present invention can be prepared. The oxidation method exemplified herein can easily be adapted to the compounds of the present invention by those skilled in the art.

To a stirred mixture of N-[4-chloro-3-(trifluoromethyl) phenyl]-N'-{4-[2-(N-methylcarbamoyl)(4-pyridyloxy)]phenyl} urea (500 mg, 1.08 mmol), in a mixture of anh $CH_2Cl_2$ (2.2 mL) and anh THF (2.2 mL) was added 3-chloroperbenzoic acid (77% pure, 1.09 g, 4.86 mmol, 4.5 equiv.), and the resulting mixture was heated at 40° C. for 33 h. The resulting mixture was concentrated under reduced pressure, and the crude product was purified by MPLC (Biotage®; gradient from 20% acetone/hexane to 50% acetone/hexane). Recrystallization from EtOAc afforded N-[4-chloro-3-(trifluoromethyl)phenyl]-N'-{4-[2-(N-methylcarbamoyl)-1-oxo-(4-pyridyloxy)]phenyl} urea as a white solid (293 mg, 57%): mp (uncorrected) 232-234° C.; TLC (50% acetone/hexane) $R_f$ 0.13; $^1$H-NMR (DMSO-$d_6$) δ 11.48 (broad s, 1H), 9.19 (s, 1H), 8.98 (s, 1H), 8.38 (d, J=5.8 Hz, 1H), 8.10 (d, J=2.5 Hz, 1H), 7.64 (dd, J=8.2 Hz, 2.6 Hz, 1H), 7.61 (d, J=8.4 Hz, 1H), 7.57 (d, J=8.7 Hz, 2H), 7.54 (d, J=2.6 Hz, 1H), 7.28 (dd, J=5.7 Hz, 2.5 Hz, 1H), 7.18 (d, J=8.8 Hz, 2H), 2.86 (d, J=5.0 Hz, 3H); HPLC EI-MS m/z 481 ((M+H)$^+$). Anal. calcd for $C_{21}H_{16}ClFN_4O_4$: C 52.46% H 3.33% N 11.65%. Found: C 52.22% H 3.39% N 11.49%.

Experimental Synthesis 2

N-[4-chloro-3-(trifluoromethyl)phenyl]-N'-{4-[2-carbamoyl-1-oxo-(4-yridyloxy)]phenyl}urea The title compound is not a compound of this invention. It has been distinguished from the compounds of this invention by a proviso. However, its preparation illustrates how other compounds of the present invention can be prepared.

Step 1: Preparation of 4-chloro-2-pyridinecarboxamide

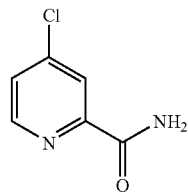

To a stirred mixture of methyl 4-chloro-2-pyridinecarboxylate hydrochloride (1.0 g, 4.81 mmol) dissolved in conc. aqueous ammonia (32 mL) was added ammonium chloride (96.2 mg, 1.8 mmol, 0.37 equiv.), and the heterogeneous reaction mixture was stirred at ambient temperature for 16 h. The reaction mixture was poured into EtOAc (500 mL) and water (300 mL). The organic layer was washed with water (2×300 mL) and a saturated NaCl solution (1×300 mL), dried (MgSO$_4$), concentrated in vacuo to give 4-chloro-2-pyridinecarboxamide as a beige solid (604.3 mg, 80.3%): TLC (50% EtOAc/hexane) $R_f$ 0.20; $^1$H-NMR (DMSO-$d_6$) δ 8.61 (d, J=5.4 Hz, 1H), 8.20 (broad s, 1H), 8.02 (d, J=1.8 Hz, 1H), 7.81 (broad s, 1H), 7.76 to 7.73 (m, 1H).

Step 2: Preparation of 4-(4-aminophenoxy)-2-pyridinecarboxamide

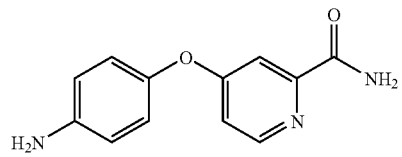

To 4-aminophenol (418 mg, 3.83 mmol) in anh DMF (7.7 mL) was added potassium tert-butoxide (447 mg, 3.98 mmol, 1.04 equiv.) in one portion. The reaction mixture was stirred at room temperature for 2 h, and a solution of 4-chloro-2-pyridinecarboxamide (600 mg, 3.83 mmol, 1.0 equiv.) in anh DMF (4 mL) was then added. The reaction mixture was stirred at 80° C. for 3 days and poured into a mixture of EtOAc and a saturated NaCl solution. The organic layer was sequentially washed with a saturated NH$_4$Cl solution then a saturated NaCl solution, dried (MgSO$_4$), and concentrated under reduced pressure. The crude product was purified using MPLC chromatography (Biotage®; gradient from 100%

EtOAc to followed by 10% MeOH/50% EtOAc/40% hexane) to give the 4-chloro-5-trifluoromethylaniline as a brown solid (510 mg, 58%). $^1$H-NMR (DMSO-d$_6$) δ 68.43 (d, J=5.7 Hz, 1H), 8.07 (br s, 1H), 7.66 (br s, 1H), 7.31 (d, J=2.7 Hz, 1H), 7.07 (dd, J=5.7 Hz, 2.7 Hz, 1H), 6.85 (d, J=9.0 Hz, 2 H), 6.62 (d, J=8.7 Hz, 2H), 5.17 (broad s, 2H); HPLC EI-MS m/z 230 ((M+H)$^+$.

Step 3: Preparation of N-[4-chloro-3-(trifluoromethyl)phenyl]-N'-{4-[2-carbamoyl-(4-pyridyloxy)]phenyl} urea

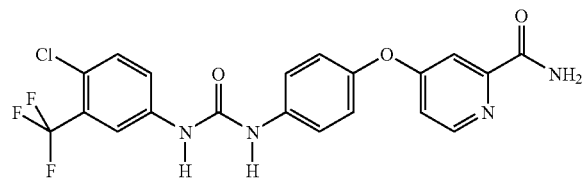

A mixture of 4-chloro-5-trifluoromethylaniline (451 mg, 2.31 mmol, 1.1 equiv.) and 1,1'-carbonyl diimidazole (419 mg, 2.54 mmol, 1.2 equiv.) in anh dichloroethane (5.5 mL) was stirred under argon at 65° C. for 16 h. Once cooled to room temperature, a solution of 4-(4-aminophenoxy)-2-pyridinecarboxamide (480 mg, 2.09 mmol) in anh THF (4.0 mL) was added, and the reaction mixture was stirred at 60° C. for 4 h. The reaction mixture was poured into EtOAc, and the organic layer was washed with water (2×) and a saturated NaCl solution (1×), dried (MgSO$_4$), filtered, and evaporated in vacuo. Purification using MPLC chromatography (Biotage®; gradient from 100% EtOAc to 2% MeOH/EtOAc) gave N-[4-chloro-3-(trifluoromethyl)phenyl]-N'-{4-[2-carbamoyl-(4-pyridyloxy)]phenyl} urea as a white solid (770 mg, 82%): TLC (EtOAc) R$_f$ 0.11, 100% ethyl acetate $^1$H-NMR (DMSO-d$_6$) δ 9.21 (s, 1H), 8.99 (s, 1H), 8.50 (d, J=5.6 Hz, 1H), 8.11 (s, 1H), 8.10 (s, 1H), 7.69 (broad s, 1H), 7.64 (dd, J=8.2 Hz, 2.1 Hz, 1H), 7.61 (s, 1H), 7.59 (d, J=8.8 Hz, 2H), 7.39 (d, J=2.5 Hz, 1H), 7.15 (d, J=8.9 Hz, 2H), 7.14 (m, 1H); MS LC-MS (MH$^+$=451). Anal. calcd for C$_{20}$H$_{14}$ClF$_3$N$_4$O$_3$: C 53.29% H 3.13% N 12.43%. Found: C 53.33% H 3.21% N 12.60%;.

N-[4-chloro-3-(trifluoromethyl)phenyl]-N'-{4-[2-carbamoyl-1-oxo-(4-pyridyloxy)]phenyl} urea

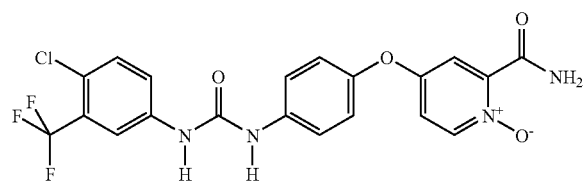

N-[4-chloro-3-(trifluoromethyl)phenyl]-N'-{4-[2-carbamoyl-1-oxo-(4-pyridyloxy)]phenyl} urea (125.6 mg, 51%) was prepared as a white solid from N-[4-chloro-3-(trifluoromethyl)phenyl]-N'-{4-[2-carbamoyl-(4-pyridyloxy)]phenyl} urea (240.0 mg, 0.53 mmol), in the manner described for N-[4-chloro-3-(trifluoromethyl)phenyl]-N'-{4-[2-(N-methylcarbamol)-1-oxo-(4-pyridyloxy)]phenyl} urea: TLC (5% MeOH/CH$_2$Cl$_2$) R$_f$ 0.17; $^1$H-NMR (DMSO-d$_6$) δ 10.72 (d, J=4.3 Hz, 1H), 9.21 (s, 1H), 8.99 (s, 1H); 8.36 (d, J=7.2 Hz, 1H), 8.31 (d, J=4.1 Hz, 1H), 8.10 (d, J=2.3 Hz, 1H), 7.65 (dd, J=8.7 Hz, 2.3 Hz, 1H), 7.60 (d, J=8.9 Hz, 1H), 7.57 (d, J=9.0 Hz, 2H), 7.54 (d, J=3.8 Hz, 1H), 7.28 (dd, J=7.2 Hz, 3.8 Hz, 1H) 7.18 (d, J =9.0 Hz, 2 H); HPLC EI-MS m/z 467 ((M+H)$^+$; Anal. calcd for C$_{20}$H$_{14}$ClF$_3$N$_4$O$_4$ 0.5H$_2$O: C 50.49% H 3.18% N 11.78%. Found. C 50.69% H 2.86% N 11.47%.

BIOLOGICAL EXAMPLES

P38 Kinase In Vitro Assay:

The in vitro inhibitory properties of compounds are determined using a p38 kinase inhibition assay. P38 activity is detected using an in vitro kinase assay run in 96-well microtiter plates. Recombinant human p38 (0.5 μg/mL) is mixed with substrate (myelin basic protein, 5 μg/mL) in kinase buffer (25 mM Hepes, 20 mM MgCl$_2$ and 150 mM NaCl) and compound. One μCi/well of $^{33}$P-labeled ATP (10 μM) is added to a final volume of 100 μL. The reaction is run at 32° C. for 30 min. and stopped with a 1M HCl solution. The amount of radioactivity incorporated into the substrate is determined by trapping the labeled substrate onto negatively charged glass fiber filter paper using a 1% phosphoric acid solution and read with a scintillation counter. Negative controls include substrate plus ATP alone.

LPS Induced TNFα Production in Mice:

The in vivo inhibitory properties of selected compounds can be determined using a murine LPS induced TNFα production in vivo model. BALB/c mice (Charles River Breeding Laboratories; Kingston, N.Y.) in groups of ten are treated with either vehicle or compound by the route noted. After one hour, endotoxin (E. coli lipopolysaccharide (LPS), 100 μg) is administered intraperitoneally (i.p.). After 90 min, animals are euthanized by carbon dioxide asphyxiation and plasma is obtained from individual animals by cardiac puncture into heparinized tubes. The samples are clarified by centrifugation at 12,500×g for 5 min at 4° C. The supernatants are decanted to new tubes, which are stored as needed at −20° C., TNFα levels in sera are measured using a commercial murine TNF ELISA kit (Genzyme).

The two preceding biological examples can be used to demonstrate that the compounds are inhibiting p38 kinase in vitro and in vivo, and therefore establishes their utility in the treatment of p38 mediated diseases, such as inflammation and osteoporosis.

In Vitro raf Kinase Assay:

In an in vitro kinase assay, raf is incubated with MEK in 20 mM Tris-HCl, pH 8.2 containing 2 mM 2-mercaptoethanol and 100 mM NaCl. This protein solution (20 μL) is mixed with water (5 μL) or with compounds diluted with distilled water from 10 mM stock solutions of compounds dissolved in DMSO. The kinase reaction is initiated by adding 25 μL [γ-$^{33}$P]ATP (1000-3000 dpm/pmol) in 80 mM Tris-HCl, pH 7.5, 120 mM NaCl, 1.6 mM DTT, 16 MM MgCl$_2$. The reaction mixtures are incubated at 32° C., usually for 22 min. Incorporation of $^{33}$P into protein is assayed by harvesting the reaction onto phosphocellulose mats, washing away free counts with a 1% phosphoric acid solution and quantitating phosphorylation by liquid scintillation counting. For high throughput screening, 10 μM ATP and 0.4 μM MEK are used. In some experiments, the kinase reaction is stopped by adding an equal amount of Laemmli sample buffer Samples are boiled 3 min and the proteins resolved by electrophoresis on 7.5% Laemmli gels. Gels are fixed, dried and exposed to an imaging plate (Fuji). Phosphorylation is analyzed using a Fujix Bio-Imaging Analyzer System.

Tumor Cell Proliferation Assay:

For in vitro growth assay, human tumor cell lines, including but not limited to HCT116 and DLD-1, containing mutated K-ras genes are used in standard proliferation assays for anchorage dependent growth on plastic or anchorage independent growth in soft agar. Human tumor cell lines are obtained from ATCC (Rockville Md.) and maintained in RPMI with 10% heat inactivated fetal bovine serum and 200 mM glutamine. Cell culture media and additives are obtained from Gibco/BRL (Gaithersburg, Md.) except for fetal bovine serum (JRH Biosciences, Lenexa, Kans.). In a standard proliferation assay for anchorage dependent growth, $3 \times 10^3$ cells are seeded into 96-well tissue culture plates and allowed to attach overnight at 37° C. in a 5% $CO_2$ incubator. Compounds are titrated in media in dilution series and added to 96 well cell cultures. Cells are allowed to grow 5 days typically with a feeding of fresh compound containing media on day three. Proliferation is monitored by measuring metabolic activity with standard XTT colorimetric assay (Boehringer Mannheim) measured by standard ELISA plate reader at OD 490/560, harvesting the cells onto glass fiber mats using a cell harvester and measuring $^3$H-thymidine incorporation by liquid scintillant counting.

For anchorage independent cell growth, cells are plated at $1 \times 10^3$ to $3 \times 10^3$ in 0.4% Seaplaque agarose in RPMI complete media, overlaying a bottom layer containing only 0.64% agar in RPMI complete media in 24-well tissue culture plates. Complete media plus dilution series of compounds are added to wells and incubated at 37° C. in a 5% $CO_2$ incubator for 10-14 days with repeated feedings of fresh media containing compound at 3-4 day intervals. Colony formation is monitored and total cell mass, average colony size and number of colonies are quantitated using image capture technology and image analysis software (Image Pro Plus, media Cybernetics).

The two preceding assays establish that the compounds of Formula I are active to inhibit raf kinase activity and to inhibit oncogenic cell growth.

KDR (VEGFR2) Assay:

The cytosolic kinase domain of KDR kinase is expressed as a 6His fusion protein in Sf9 insect cells. The KDR kinase domain fusion protein is purified over a Ni++ chelating column. Ninety-six well ELISA plates are coated with 5 μg poly(Glu4;Tyr1) (Sigma Chemical Co., St Louis, Mo.) in 100 μl HEPES buffer (20 mM HEPES, pH 7.5, 150 mM NaCl, 0.02% Thimerosal) at 4° overnight. Before use, the plate is washed with HEPES, NaCl buffer and the plates are blocked with 1% BSA, 0.1% Tween 20 in HEPES, NaCl buffer.

Test compounds are serially diluted in 100% DMSO from 4 mM to 0.12 μM in half-log dilutions. These dilutions are further diluted twenty fold in H2O to obtain compound solutions in 5% DMSO. Following loading of the assay plate with 85 μl of assay buffer (20 mM HEPES, pH 7.5, 100 mM KCl, 10 mM $MgCl_2$, 3 mM $MnCl_2$, 0.05% glycerol, 0.005% Triton X-100, 1 mM -mercaptoethanol, with or without 3.3 μM ATP), 5 μl of the diluted compounds are added to a final assay volume of 100 μl. Final concentrations are between 10 μM, and 0.3 nM in 0.25% DMSO. The assay is initiated by the addition of 10 μl (30 ng) of KDR kinase domain.

The assay is incubated with test compound or vehicle alone with gentle agitation at room temperature for 60 minutes. The wells are washed and phosphotyrosines (PY) are probed with an anti-phosphotyrosine (PY), mAb clone 4G10 (Upstate Biotechnology, Lake Placid, N.Y.). PY/anti-PY complexes are detected with an anti-mouse IgG/HRP conjugate (Amersham International plc, Buckinghamshire, England). Phosphotyrosine is quantitated by incubating with 100 μl 3,3',5,5'tetramethylbenzidine solution (Kirkegaard and Perry, TMB Microwell 1 Component peroxidase substrate). Color development is arrested by the addition of 100 μl 1% HCl-based stop solution (Kirkegaard and Perry, TMB 1 Component Stop Solution).

Optical densities are determined spectrophotometrically at 450 nm in a 96-well plate reader, SpectraMax 250 (Molecular Devices). Background (no ATP in assay) OD values are subtracted from all ODs and the percent inhibition is calculated according to the equation:

$$\% \text{ Inhibition} = \frac{\left(\frac{OD(\text{vehicle control}) - }{OD(\text{with compound})}\right) \times 100}{OD(\text{vehicle control}) - OD(\text{no } ATP \text{ added})}$$

The $IC_{50}$ values are determined with a least squares analysis program using compound concentration versus percent inhibition.

Cell Mechanistic Assay-Inhibition of 3T3 KDR Phosphorylation:

NIH3T3 cells expressing the full length KDR receptor are grown in DMEM (Life Technologies, Inc., Grand Island, N.Y.) supplemented with 10% newborn calf serum, low glucose, 25 mM/L sodium pyruvate, pyridoxine hydrochloride and 0.2 mg/ ml of G418 (Life Technologies Inc., Grand Island, N.Y.). The cells are maintained in collagen I-coated T75 flasks (Becton Dickinson Labware, Bedford, Mass.) in a humidified 5% CO2 atmosphere at 37° C.

Fifteen thousand cells are plated into each well of a collagen I-coated 96-well plate in the DMEM growth medium. Six hours later, the cells are washed and the medium is replaced with DMEM without serum. After overnight culture to quiesce the cells, the medium is replaced by Dulbecco's phosphate-buffered saline (Life Technologies Inc., Grand Island, N.Y.) with 0.1% bovine albumin (Sigma Chemical Co., St Louis, Mo.).

After adding various concentrations (0-300 nM) of test compounds to the cells in 1% final concentration of DMSO, the cells are incubated at room temperature for 30 minutes. The cells are then treated with VEGF (30 ng/ml) for 10 minutes at room temperature. Following VEGF stimulation, the buffer is removed and the cells are lysed by addition of 150 μl of extraction buffer (50 mM Tris, pH 7.8, supplemented with 10% glycerol, 50 mM BGP, 2 mM EDTA, 10 mM NaF, 0.5 mM NaVO4, and 0.3% TX-100) at 4° C. for 30 minutes.

To assess receptor phosphorylation, 100 microliters of each cell lysate is added to the wells of an ELISA plate precoated with 300 ng of antibody C20 (Santa Cruz Biotechnology, Inc., Santa Cruz, Calif.). Following a 60-minute incubation, the plate is washed and bound KDR is probed for phosphotyrosine using an anti-phosphotyrosine mAb clone 4G10 (Upstate Biotechnology, Lake Placid, N.Y.). The plate is washed and wells are incubated with anti-mouse IgG/HRP conjugate (Amersham International plc, Buckinghamshire, England) for 60 minutes. Wells are washed and phosphotyrosine is quantitated by addition of 100 μl per well of 3,3',5, 5'tetramethylbenzidine (Kirkegaard and Perry, TMB Microwell 1 Component peroxidase substrate) solution. Color development is arrested by the addition of 100 μl 1% HCl based stop solution (Kirkegaard and Perry, TMB 1 Component Stop Solution).

Optical densities (OD) are determined spectrophotometrically at 450 nm in a 96-well plate reader (SpectraMax 250, Molecular Devices). Background (no VEGF added) OD values are subtracted from all ODs and percent inhibition is calculated according to the equation:

$$\% \text{ Inhibition} = \frac{\left(\begin{array}{c}OD(VEGF \text{ control}) - \\ OD(\text{with test compound})\end{array}\right) \times 100}{OD(VEGF \text{ control}) - OD(\text{no } VEGF \text{ added})}$$

IC$_{50}$s are determined on some of the exemplary materials with a least squares analysis program using compound concentration versus percent inhibition.

In Vivo Assay of VEGFR Inhibition: Matrigel® Angiogenesis Model:

Preparation of Matrigel Plugs and in vivo Phase: Matigel® (Collaborative Biomedical Products, Bedford, Mass.) is a basement membrane extract from a murine tumor composed primarily of laminin, collagen IV and heparan sulfate proteoglycan. It is provided as a sterile liquid at 4° C., but rapidly forms a solid gel at 37° C.

Liquid Matrigel at 4° C. is mixed with SK-MEL2 human tumor cells that are transfected with a plasmid containing the murine VEGF gene with a selectable marker. Tumor cells are grown in vitro under selection and cells are mixed with cold liquid Matrigel at a ratio of 2×10$^6$ per 0.5 ml. One half milliliter is implanted subcutaneously near the abdominal midline using a 25 gauge needle. Test compounds are dosed as solutions in Ethanol/Cremaphor EL/saline (12.5%:12.5%:75%) at 30, 100, and 300 mg/kg po once daily starting on the day of implantation. Mice are euthanized 12 days post-implantation and the Matrigel pellets are harvested for analysis of hemoglobin content.

Hemoglobin Assay: the Matrigel pellets are placed in 4 volumes (w/v) of 4° C. Lysis Buffer (20 mM Tris pH 7.5, 1 mM EGTA, 1 mM EDTA, 1% Triton X-100 [EM Science, Gibbstown, N.J.], and complete, EDTA-free protease inhibitor cocktail [Mannheim, Germany]), and homogenized at 4° C. Homogenates are incubated on ice for 30 minutes with shaking and centrifuged at 14K×g for 30 minutes at 4° C. Supernatants are transferred to chilled microfuge tubes and stored at 4° C. for hemoglobin assay.

Mouse hemoglobin (Sigma Chemical Co., St. Louis, Mo.) is suspended in autoclaved water (BioWhittaker, Inc, Walkersville, Md.) at 5 mg/ml. A standard curve is generated from 500 micrograms/ml to 30 micrograms/ml in Lysis Buffer (see above). Standard curve and lysate samples are added at 5 microliters/well in duplicate to a polystyrene 96-well plate. Using the Sigma Plasma Hemoglobin Kit (Sigma Chemical Co., St. Louis, Mo.), TMB substrate is reconstituted in 50 mls room temperature acetic acid solution. One hundred microliters of substrate is added to each well, followed by 100 microliters/well of Hydrogen Peroxide Solution at room temperature. The plate is incubated at room temperature for 10 minutes.

Optical densities are determined spectrophotometrically at 600 nm in a 96-well plate reader, SpectraMax 250 Microplate Spectrophoto-meter System (Molecular Devices, Sunnyvale, Calif.). Background Lysis Buffer readings are subtracted from all wells.

Total sample hemoglobin content is calculated according to the following equation:

Total Hemoglobin=(Sample Lysate Volume)×(Hemoglobin Concentration)

The average Total Hemoglobin of Matrigel samples without cells is subtracted from each Total Hemoglobin Matrigel sample with cells. Percent inhibition is calculated according to the following equation:

$$\% \text{ Inhibition} = \frac{\left(\begin{array}{c}\text{Average Total Hemoglobin} \\ \text{Drug-Treated Tumor Lysates}\end{array}\right) \times 100}{\left(\begin{array}{c}\text{Average Total Hemoglobin} \\ \text{Non-Treated}\end{array}\right)}$$

The three preceding assays establish that the compounds of Formula I are active to inhibit VEGF receptor kinase activity and to inhibit angiogenesis.

In Vivo Assay of Antitumor Activity:

An in vivo assay of the inhibitory effect of the compounds on tumors (e.g., solid cancers) mediated by raf kinase can be performed as follows: CDI nu/nu mice (6-8 weeks old) are injected subcutaneously into the flank at 1×10$^6$ cells with human colon adenocarcinoma cell line. The mice are dosed i.p., i.v. or p.o. at 10, 30, 100, or 300 mg/Kg beginning on approximately day 10, when tumor size is between 50-100 mg. Animals are dosed for 14 consecutive days; tumor size is monitored with calipers twice a week. The inhibitory effect of the compounds on p38, raf and VEGFR kinases and therefore on tumor growth (e.g., solid cancers) can further be demonstrated in vivo according to the technique of Monia et al. (*Nat. Med.* 1996, 2, 668-75).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

The invention claimed is:

1. A compound of formula (I) or a salt, prodrug or isolated stereoisomer thereof

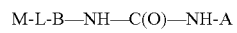

M-L-B—NH—C(O)—NH-A     I wherein A is selected from the group consisting of:
(i) phenyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $COR^1$, $COOR^1$, $CONR^1R^2$, $NR^1C(O)R^2$ halogen, cyano, and nitro;
(ii) naphthyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $COR^1$, $COOR^1$, $CONR^1R^2$, $NR^1C(O)R^2$, halogen, cyano, and nitro;
(iii) 5 and 6 membered monocyclic heteroaryl, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $COR^1$, $COOR^1$, $CONR^1R^2$, $NR^1COR^2$, halogen, cyano, and nitro; and
(iv) 8-10 membered bicyclic heteroaryl, having 1-6 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $COR^1$, $COOR^1$, $CONR^1R^2$, $NR^1COR^2$, halogen, cyano, and nitro;

B is selected from the group consisting of:
(i) phenylene, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro;
(ii) naphthylene, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro;
(iii) 5 and 6 membered monocyclic heteroaryl-ene, having 1-3 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro; and
(iv) 8-10 membered bicyclic heteroaryl-ene, having 1-6 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro;

L is selected from the group consisting of:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^{3a}$—$(CH_2)_l$—,
(e) —$(CH_2)_m$—$NR^{3a}C(O)$—$(CH_2)_l$—,
(f) —$(CH_2)_m$—S—$(CH_2)_l$—,
(g) —$(CH_2)_m$—$C(O)NR^{3a}$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—,
(k) —$(CH_2)_m$—$CR^{3a}(OH)$—$(CH_2)_l$—;
(l) —$(CH_2)_m$—C≡C—$(CH_2)_l$—;
(m) —$(CH_2)_m$—C=C—$(CH_2)_l$—;
(n) a single bond; and
(o) —$(CH_2)_m$—$CR^{3a}R^{3b}(CH_2)_l$—;
wherein m and l are integers independently selected from 0-4;

M is selected from the group consisting of:
(a) pyridine-1-oxide substituted 1 to 3 times by a substituent selected from the group consisting of —C(O)$NR^4R^5$, —$C(NR^4)R^5$, —$C(O)R^4$, —$SO_2R^4$, and —$SO_2NR^4R^5$; which is optionally additionally substituted by $Z_r$;
(b) quinoline-1-oxide, which is optionally substituted by $Z_n$; and
(c) isoquinoline-1-oxide, which is optionally substituted by $Z_n$;
wherein r is 0-2, n is 0-3, and each Z is independently selected from the group consisting of $R^4$, halogen, cyano, —$CO_2R^4$, —$C(O)R^4$, —$C(O)NR^4R^5$, —$NO_2$, —$OR^4$, —$NR^4R^5$, —$NR^4C(O)OR^5$, —$NR^4C(O)R^5$, —$S(O)_pR^4$, and —$SO_2NR^4R^5$
wherein each $R^1$, $R^2$, $R^4$ and $R^5$ is independently selected from the group consisting of:
(a) hydrogen,
(b) $C_1$-$C_5$ linear, branched, or cyclic alkyl,
(c) phenyl,
(d) 5-6 membered monocyclic heteroaryl heteroaryl having 1-4 heteroatoms selected from the group consisting of O, N and S or 8-10 membered bicyclic heteroaryl having 1-6 heteroatoms selected from the group consisting of O, N and S,
(e) $C_1$-$C_3$ alkyl-phenyl,
(f) $C_1$-$C_3$ alkyl heteroaryl having 1-4 heteroatoms selected from the group consisting of O, N and S, said heteroaryl including 5-6 membered monocyclic and 8-10 membered bicyclic heteroaryl, and
(g) up to per-halo substituted $C_1$-$C_5$ linear or branched alkyl; and
wherein each $R^1$, $R^2$, $R^4$ and $R^5$, when not hydrogen or perhalo substituted $C_1$-$C_5$ linear or branched alkyl, are optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, amino, $C_1$-$C_3$ alkylamino, $C_1$-$C_6$ dialkylamino, halogen, cyano, and nitro;
wherein each $R^{3a}$ and $R^{3b}$ is hydrogen or $C_1$-$C_5$ linear or branched alkyl;
and p and q are integers each independently selected from 0, 1, or 2
subject to the proviso that formula I does not include compounds of formula II:

wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$X^1$ to $X^7$ are each, independently, H, OH or $O(CO)C_1$-$C_4$ alkyl.

2. A compound as in claim 1 wherein A and B of formula I, are each independently:
a substituted or unsubstituted phenyl group,
a substituted or unsubstituted a naphthyl group,
a substituted or unsubstituted monocyclic heteroaryl group selected from the group consisting of 2-furyl, 3-furyl, 2-thienyl, 3-thienyl, 2-triazinyl, 4triazinyl, 1-pyrrolyl, 2-pyrrolyl, 3-pyrrolyl, 1-imidazolyl 2-imidazolyl, 4-imidazolyl, 5-imidazolyl, 1-pyrazolyl, 3-pyrazolyl, 4-pyrazolyl, 5-pyrazolyl, 3-isoxazolyl, 4-isoxazolyl, 5-isoxazolyl, 2-oxazolyl, 4-oxazolyl, 5-oxazolyl, 3-oxazolyl, 2-thiazolyl, 4-thiazolyl, 5-thiazolyl, 3-isothiazolyl, 4-isothiazolyl, 5-isothiazolyl, 2-pyridyl, 3-pyridyl, 4-pyridyl, 2-pyrimidinyl, 4-pyrimidinyl, 5-pyrimidinyl, 6-pyrimidinyl, 1,2,3-triazol-1-yl, 1,2,3-triazol-4-yl, 1,2,3-triazol-5-yl, 1,2,4-triazol-1-yl, 1,2,3-triazol-3-yl, 1,2,3-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-oxadiazol-3-yl, 1,2,4-oxadiazol-5-yl, 1,3,4-thiadiazol-2-yl, 1,3,4-thiadiazol-5-yl, 1,3,4-thiadiazol-3-yl, 1,2,3-thiadiazol-4-yl, 1,2,3-thiadiazol-5-yl, 3-pyridazinyl-, 4-pyridazinyl, 2-pyrazinyl and 3-pyrazinyl or a substituted or unsubstituted bicyclic heteroaryl group selected from the group consisting of 2-, 3-, 4-, 5-, 6- and 7-benzofuryl, 2-, 3-, 4-, 5-, 6- and 7-benzothienyl, 1-, 2-, 3-, 4-, 5-, 6- and 7-indolyl, 1-, 2-, 3-, 4-, 5-, 6- or 7-isoindolyl, 1-, 2-, 4- and 5-benzimidazolyl, 1-, 3-, 4-, 5-, 6- and 7-indazolyl (benzopyrazolyl), 2-, 4-, 5-, 6- and 7-benzoxazolyl, 3-, 4-, 5- 6- and 7-benzisoxazolyl, 1-, 3-, 4-, 5-, 6- and 7-benzothiazolyl, 2-, 4-, 5-, 6- and 7-benzisothiazolyl, 2-, 4-, 5-, 6- and 7-benz-1,3-oxadiazolyl, 2-, 3-, 4-, 5-, 6-, 7- and 8-quinolinyl, 1-, 3-, 4-, 5-, 6-, 7-, 8-isoquinolinyl, and 2-, 4-, 5-, 6-, 7- and 8-quinazolinyl.

3. A compound as in claim 1 wherein A of formula I is a substituted or unsubstituted phenyl group, a substituted or unsubstituted a naphthyl group, a substituted or unsubstituted monocyclic heteroaryl group selected from the group consisting of 2-furyl, 3-furyl, 2-thienyl, 3-thienyl, 2-triazinyl, 4-triazinyl, 1-pyrrolyl, 2-pyrrolyl, 3-pyrrolyl, 1-imidazolyl 2-imidazolyl, 4-imidazolyl, 5-imidazolyl, 1-pyrazolyl, 3-pyrazolyl, 4-pyrazolyl, 5-pyrazolyl, 3-isoxazolyl, 4-isoxazolyl, 5-isoxazolyl, 2-oxazolyl, 4-oxazolyl, 5-oxazolyl, 3-oxazolyl, 2-thiazolyl, 4-thiazolyl, 5-thiazolyl, 3-isothiazolyl, 4-isothiazolyl, 5-isothiazolyl, 2-pyridyl, 3-pyridyl, 4-pyridyl, 2-pyrimidinyl, 4-pyrimidinyl, 5-pyrimidinyl, 6-pyrimidinyl, 1,2,3-triazol-1-yl, 1,2,3-triazol-4-yl, 1,2,3-triazol-5-yl, 1,2,4-triazol-1-yl, 1,2,3-triazol-3-yl, 1,2,3-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-oxadiazol-3-yl, 1,2,4-oxadiazol-5-yl, 1,3,4-thiadiazol-2-yl, 1,3,4-thiadiazol-5-yl, 1,3,4-thiadiazol-3-yl, 1,2,3-thiadiazol-4-yl, 1,2,3-thiadiazol-5-yl, 3-pyridazinyl-, 4-pyridazinyl, 2-pyrazinyl and 3-pyrazinyl or a substituted or unsubstituted bicyclic heteroaryl group selected from the group consisting of 2-, 3-, 4-, 5-, 6- and 7-benzofuryl, 2-, 3-, 4-, 5-, 6- and 7-benzothienyl, 1-, 2-, 3-, 4-, 5-, 6- and 7-indolyl, 1-, 2-, 4- and 5-benzimidazolyl, 1-, 3-, 4-, 5-, 6- and 7-indazolyl (benzopyrazolyl), 2-, 4-, 5-, 6- and 7-benzoxazolyl, 3-, 4-, 5- 6- and 7-benzisoxazolyl, 1-, 3-, 4-, 5-, 6- and 7-benzothiazolyl, 2-, 4-, 5-, 6- and 7-benzisothiazolyl, 2-, 4-, 5-, 6- and 7-benz-1,3-oxadiazolyl, 2-, 3-, 4-, 5-, 6-, 7- and 8-quinolinyl, 1-, 3-, 4-, 5-, 6-, 7-, 8-isoquinolinyl, and 2-, 4-, 5-, 6-, 7- and 8-quinazolinyl and B of formula I is a substituted or unsubstituted phenyl group, a substituted or unsubstituted monocyclic heteroaryl group selected from the group consisting of 2- furyl, 3-furyl, 2-thienyl, 3-thienyl, 2-triazinyl, 4-triazinyl, 1-pyrrolyl, 2-pyrrolyl, 3-pyrrolyl, 1-imidazolyl 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 3-oxazolyl, 2-thiazolyl, 4-thiazolyl, 5-thiazolyl, 3-isothiazolyl, 4-isothiazolyl, 5-isothiazolyl, 2-pyridyl, 3-pyridyl, 4-pyridyl, 2-pyrimidinyl, 4-pyrimidinyl, 5-pyrimidinyl, 6-pyrimidinyl, 1,2,3-triazol-1-yl, 1,2,3-triazol-4-yl, 1,2,3-triazol-5-yl, 1,2,4-triazol-1-yl, 1,2,3-triazol-3-yl, 1,2,3-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-oxadiazol-3-yl, 1,2,4-oxadiazol-5-yl, 1,3,4-thiadiazol-2-yl, 1,3,4-thiadiazol-5-yl, 1,3,4-thiadiazol-3-yl, 1,2,3-thiadiazol-4-yl, 1,2,3-thiadiazol-5-yl, 3-pyridazinyl-, 4-pyridazinyl, 2-pyrazinyl and 3-pyrazinyl or a substituted or unsubstituted bicyclic heteroaryl group selected from the group consisting of 2-, 3-, 4-, 5-, 6- and 7-benzofuryl, 2-, 3-, 4-, 5-, 6- and 7-benzothienyl, 1-, 2-, 3-, 4-, 5-, 6- and 7-indolyl, 1-, 2-, 4- and 5-benzimidazolyl, 1-, 3-, 4-, 5-, 6- and 7-indazolyl (benzopyrazolyl), 2-, 4-, 5-, 6- and 7-benzoxazolyl, 3-, 4-, 5- 6- and 7-benzisoxazolyl, 1-, 3-, 4-, 5-, 6- and 7-benzothiazolyl, 2-, 4-, 5-, 6- and 7-benzisothiazolyl, 2-, 4-, 5-, 6- and 7-benz-1,3-oxadiazolyl, 2-, 3-, 4-, 5-, 6-, 7- and 8-quinolinyl7 1-, 3-, 4-, 5-, 6-, 7-, 8-isoquinolinyl, and 2-, 4-, 5-, 6-, 7- and 8-quinazolinyl.

4. A compound as in claim 1 wherein

A of formula I is a substituted or unsubstituted group selected from the group consisting of phenyl, naphthyl, furyl, isoindolyl, oxadiazolyl, oxazolyl, isooxazolyl, indolyl, indazolyl, benzothiazolyl, benzimidazolyl, benzoxazolyl, pyrazolyl, pyridinyl, pyrimidinyl, pyrrolyl, quinolinyl, isoquinolinyl, tetrazolyl, thiadiazolyl, thiazolyl and thienyl, B of formula I is a substituted or unsubstituted group selected from the group consisting of phenylene, naphthylene, thienylene, furylene, pyridine-ene, quinoline-ene, isoquinoline-ene and indole-ene, L is selected from the group consisting of —CH$_2$O—, —OCH$_2$—, —O—, a single bond, —CH$_2$—, —NH—, —N(CH$_3$)—, —N(CH$_3$)CH$_2$—, —NC$_2$H$_4$—, —C(O)—, —NHCH$_2$—, —N(CH$_3$)C(O)—, —NHC(O)—, —CH$_2$N(Cl$_3$)—, —C(O)NH—, —CH$_2$S—, —SCH$_2$—, —S—, —C(O)NCH$_3$—, —CH$_2$C(O)N(CH$_3$)—, —C(O)N(CH$_3$)CH$_2$—, —CF$_2$—, —CCl$_2$—, —CHF— and —CH(OH)—, and M is defined as in claim 1.

5. A compound as in claim 1 wherein

A of formula I is a substituted or unsubstituted group selected from the group consisting of phenyl, naphthyl, furyl, isoindolyl, oxadiazolyl, oxazolyl, isoxazolyl, indolyl, indazolyl, benzothiazolyl, benzimidazolyl, benzoxazolyl, pyrazolyl, pyridinyl, pyrimidinyl, pyrrolyl, quinolinyl, isoquinolinyl, tetrazolyl, thiadiazolyl, thiazolyl and thienyl, B of formula I is a substituted or unsubstituted group selected from the group consisting of phenylene, thienylene, furylene, pyridine-ene, quinoline-ene, isoquinoline-ene and indole-ene, L is selected from the group consisting of —CH$_2$O—, —OCH$_2$—, —O—, a single bond, —CH$_2$—, —NH—, —N(CH$_3$)—, —N(CH$_3$)CH$_2$—, —NC$_2$H$_4$—, —C(O)—, —NHCH$_2$—, —N(CH$_3$)C(O)—, —NHC(O)—, —CH$_2$N(CH$_3$)—, —C(O)NH—, —CH$_2$S—, —SCH$_2$—, —S—, —C(O)NCH$_3$—, —CH$_2$C(O)N(CH$_3$)—, —C(O)N(CH$_3$)CH$_2$—, —CF$_2$—, —CCl$_2$—, —CHF— and —CH(OH)—, and M is defined as in claim 1.

6. A compound as in claim 4 wherein

A of formula I is a substituted group and the substituents are selected from the group consisting of methyl, trifluoromethyl, ethyl, n-propyl, n-butyl, n-pentyl, i-propyl, t-butyl, N(C$_1$-C$_5$ alkyl)(C$_1$-C$_5$ alkyl);
N(C$_1$-C$_5$ alkyl)(phenyl);
N(C$_{1-5}$ alkyl)(pyridinyl);
S(O)$_2$(C$_1$-C$_5$ alkyl);
SO$_2$NH(C$_1$-C$_5$ alkyl);
SO$_2$N(C$_1$-C$_5$ alkyl)(C$_1$-C$_5$ alkyl);

NHSO$_2$(C$_1$-C$_5$ alkyl);
N(C$_1$-C$_3$ alkyl)SO$_2$(C$_1$-C$_5$ alkyl);
CO(C$_1$-C$_6$ alkyl);
CO(phenyl);
CO(pyridinyl);
COO(C$_1$-C$_6$alkyl);
COO(phenyl);
COO(pyridinyl);
COOH;
CONH$_2$;
CONH(C$_1$-C$_6$ alkyl);
CONH(phenyl);
CONH(pyridinyl);
CON(C$_1$-C$_6$alkyl);
CON(phenyl);
CON(pyridinyl);
NHCO(C$_1$-C$_5$ alkyl);
NHCO(phenyl);
NHCO(pyridinyl); and
N(C$_1$-C$_5$ alkyl)CO(C$_1$-C$_5$ alkyl).

7. A compound as in claim 1 wherein
A of formula I is a substituted or unsubstituted group selected from the group consisting of phenyl, pyridinyl, pyrimidinyl, pyrazolyl, quinolinyl, isoquinolinyl, isoindolyl, pyrrolyl, indazolyl, thienyl, furyl and isoxazolyl and
B of formula I is a substituted or unsubstituted group selected from the group consisting of phenylene, naphthylene, thienylene, furylene, pyridine-ene, quinoline-ene, isoquinoline-ene and indole-ene.

8. A compound as in claim 1 wherein
A of formula I is a substituted or unsubstituted group selected from the group consisting of phenyl, pyridinyl, pyrimidinyl, pyrazolyl, quinolinyl, isoquinolinyl, isoindolyl, pyrrolyl, indazolyl, thienyl, furyl and isoxazolyl and
B of formula I is a substituted or unsubstituted group selected from the group consisting of phenylene, thienylene, furylene, pyridine-ene, isoquinoline-ene and indole-ene.

9. A compound as in claim 1 wherein
A of formula I is a substituted or unsubstituted group selected from the group consisting of phenyl, pyridinyl, pyrimidinyl, pyrazolyl, quinolinyl, isoquinolinyl, isoindolyl, pyrrolyl, indazolyl, thienyl, furyl and isoxazolyl and
B of formula I is a substituted or unsubstituted group selected from the group consisting of phenylene and pyridine-ene.

10. A compound as in claim 7 wherein
A of formula I is a substituted group and the substituents are selected from the group consisting of:
NH(C$_1$-C$_5$ alkyl);
NH(phenyl);
NH(pyridinyl);
A=phenyl, B=phenylene,
A=phenyl, B=pyridinyl-ene,
A=phenyl, B=isoquinolinyl-ene,
A=pyridinyl, B=phenylene,
A=pyridinyl, B=pyridinyl-ene,
A=pyridinyl, B=isoquinolinyl-ene,
A=naphthyl, B=phenylene,
A=naphthyl, B=pyridinyl-ene,
A=naphthyl, B=isoquinolinyl-ene,
A=isoquinolinyl, B=phenylene,
A=isoquinolinyl, B=pyridinyl-ene,
A=isoquinolinyl, B=isoquinolinyl-ene,
A=quinolinyl, B=phenylene,
A=quinolinyl, B=pyridinyl-ene,
A=quinolinyl, B=isoquinolinyl-ene,
A=pyrazolyl, B=phenylene,
A=pyrazolyl, B=pyridinyl-ene,
A=pyrazolyl, B=isoquinolinyl-ene,
A=isoxazolyl, B=phenylene,
A=isoxazolyl, B=pyridinyl-ene,
A=isoxazolyl, B=isoquinolinyl-ene.
A=indazolyl, B=phenylene,
A=indazolyl, B=pyridinyl-ene,
and
A=indazolyl, B=isoquinolinyl-ene.

11. A compound of formula I of claim 1 wherein in A, and B are one of the following combinations and M is as defined in claim 1:
methylethyl, methyipropyl, cyclopropyl, cyclobutyl, cyclopentyl, methoxy, ethoxy, propoxy, butyoxy, pentoxy, methyl sulfonyl, trifluoromethyl sulfonyl, Cl, Br, F, cyano, nitro, hydroxy, amino, methylamino, dimethylamino, ethylamino and diethylamino.

12. A compound of formula I of claim 1, wherein in A, and B are one of the following combinations and M is as defined in claim 1:
A=phenyl, B=phenylene, and
A=phenyl, B=pyridinyl-ene.

13. A compound of formula (I) or a salt, or isolated stereoisomer thereof

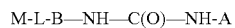

M-L-B—NH—C(O)—NH-A        I wherein A is selected from the group consisting of:
(i) phenyl, optionally substituted with 1-3 substituents independently selected from the group consisting of R$^1$, OR$^1$, NR$^1$R$^2$, S(O)$_q$R$^1$, SO$_2$NR$^1$R$^2$, NR$^1$SO$_2$R$^2$, COR$^1$, COOR$^1$, CONR$^1$R$^2$, NR$^1$C(O)R$^2$, halogen, cyano, and nitro;
(ii) naphthyl, optionally substituted with 1-3 substituents independently selected from the group consisting of R$^1$, OR$^1$, NR$^1$R$^2$, S(O)$_q$R$^1$, SO$_2$NR$^1$R$^2$, NR$^1$SO$_2$R$^2$, COR$^1$, COOR$^1$, CONR$^1$R$^2$, NR$^1$C(O)R$^2$, halogen, cyano, and nitro;
(iii) 5 and 6 membered monocyclic heteroaryl, having 1-3 heteroatoms independently selected from the group consisting of O, N and S, optionally substituted with 1-3 substituents independently selected from the group consisting of R$^1$, OR$^1$, NR$^1$R$^2$, S(O)$_q$R$^1$, SO$_2$NR$^1$R$^2$, NR$^1$SO$_2$R$^2$, COR$^1$, COOR$^1$, CONR$^1$R$^2$, NR$^1$COR$^2$, halogen, cyano, and nitro; and
(iv) 8-10 membered bicyclic heteroaryl, having 1-6 heteroatoms independently selected from the group consisting of O, N and S, optionally substituted with 1-3 substituents independently selected from the group consisting of R$^1$, OR$^1$, NR$^1$R$^2$, S(O)$_q$R$^1$, SO$_2$NR$^1$R$^2$, NR$^1$SO$_2$R$^2$, COR$^1$, COOR$^1$, CONR$^1$R$^2$, NR$^1$COR$^2$, halogen, cyano, and nitro;
B is selected from the group consisting of:
(i) phenylene, optionally substituted with 1-3 substituents independently selected from the group consisting of C$_1$-C$_5$ linear or branched alkyl, C$_1$-C$_5$ linear or branched haloalkyl, C$_1$-C$_3$ alkoxy, hydroxy, amino, C$_1$-C$_3$ alkylamino, C$_1$-C$_3$ dialkylamino, halogen, cyano, and nitro;
(ii) naphthylene, optionally substituted with 1-3 substituents independently selected from the group consisting of C$_1$-C$_5$ linear or branched alkyl, C$_1$-C$_5$ linear or branched haloalkyl, C$_1$-C$_3$ alkoxy, hydroxy, amino, C$_1$-C$_3$ alkylamino, C$_1$-C$_3$ dialkylamino, halogen, cyano, and nitro;

(iii) 5 and 6 membered monocyclic heteroaryl-ene, having 1-3 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro; and (iv) 8-10 membered bicyclic heteroaryl-ene, having 1-6 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_3$ dialkylamino, halogen, cyano, and nitro;

L is selected from the group consisting of:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^{3a}$—$(CH_2)_l$—,
(e) —$(CH_2)_m$—$NR^{3a}$C(O)—$(CH_2)_l$—,
(f) —$(CH_2)_m$—S—$(CH_2)_l$—,
(g) —$(CH_2)_m$—C(O)$NR^{3a}$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—,
(k) —$(CH_2)_m$—$CR^{3a}$(OH)—$(CH_2)_l$—;
(l) —$(CH_2)_m$—C≡C—$(CH_2)_l$—;
(m) —$(CH_2)_m$—C═C—$(CH_2)_l$—;
(n) a single bond; and
(o) —$(CH_2)_m$—$CR^{3a}R^{3b}$—$(CH_2)_l$—;
wherein m and l are integers independently selected from 0-4;

M is selected from the group consisting of:
(a) pyridine-1-oxide substituted 1 to 3 times by a substituent selected from the group consisting of —C(O)$NR^4R^5$, —$C(NR^4)R^5$, —C(O)$R^4$, —$SO_2R^4$, and —$SO_2NR^4R^5$; which is optionally additionally substituted by $Z_r$;
(b) quinoline-1-oxide, which is optionally substituted by $Z_n$; and
(c) isoquinoline-1-oxide, which is optionally substituted by $Z_n$;
wherein r is 0-2, n is 0-3, and each Z is independently selected from the group consisting of $R^4$, halogen, cyano, —$CO_2R^4$, —C(O)$R^4$, —C(O)$NR^4R^5$, —$NO_2$, —$OR^4$, —$NR^4R^5$, —$NR^4$C(O)$OR^5$, —$N^4$C(O)$R^5$, —S(O)$_pR^4$, and —$SO_2NR^4R^5$
wherein each $R^1$, $R^2$, $R^4$ and $R^5$ is independently selected from the group consisting of:
(a) hydrogen,
(b) $C_1$-$C_5$ linear, branched, or cyclic alkyl,
(c) phenyl,
(d) 5-6 membered monocyclic heteroaryl heteroaryl having 1-4 heteroatoms selected from the group consisting of O, N and S or 8-10 membered bicyclic heteroaryl having 1-6 heteroatoms selected from the group consisting of O, N and S,
(e) $C_1$-$C_3$ alkyl-phenyl,
(f) $C_1$-$C_3$ alkyl heteroaryl having 1-4 heteroatoms selected from the group consisting of O, N and S, said heteroaryl including 5-6 membered monocyclic and 8-10 membered bicyclic heteroaryl, and
(g) up to per-halo substituted $C_1$-$C_5$ linear or branched alkyl; and wherein each $R^1$, $R^2$, $R^4$ and $R^5$, when not hydrogen or perhalo substituted $C_1$-$C_5$ linear or branched alkyl, are optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, amino, $C_1$-$C_3$ alkylamino, $C_1$-$C_6$ dialkylamino, halogen, cyano, and nitro;

wherein each $R^{3a}$ and $R^{3b}$ is hydrogen or $C_1$-$C_5$ linear or branched alkyl;

and p and q are integers each independently selected from 0, 1, or 2 subject to the proviso that formula I does not include compounds of formula II:

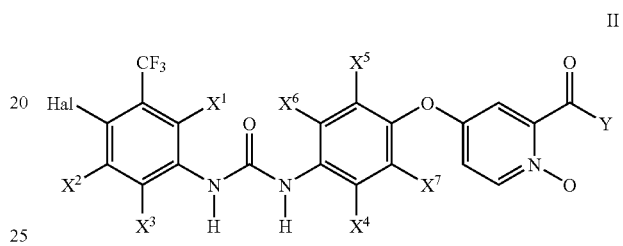

II wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$X^1$ to $X^7$ are each, independently, H, OH or O(CO)$C_1$-$C_4$ alkyl.

14. A compound as in claim 13 wherein A and B of formula I, are each independently:
a substituted or unsubstituted phenyl group,
a substituted or unsubstituted a naphthyl group,
a substituted or unsubstituted monocyclic heteroaryl group selected from the group consisting of 2-furyl, 3-furyl, 2-thienyl, 3-thienyl, 2-triazinyl, 4-triazinyl, 1-pyrrolyl, 2-pyrrolyl, 3-pyrrolyl, 1-imidazolyl 2-imidazolyl, 4-imidazolyl, 5-imidazolyl, 1-pyrazolyl, 3-pyrazolyl, 4-pyrazolyl, 5-pyrazolyl, 3-isoxazolyl, 4-isoxazolyl, 5-isoxazolyl, 2-oxazolyl, 4-oxazolyl, 5-oxazolyl, 3-oxazolyl, 2-thiazolyl, 4-thiazolyl, 5-thiazolyl, 3-isothiazolyl, 4-isothiazolyl, 5-isothiazolyl, 2-pyridyl, 3-pyridyl, 4-pyridyl, 2-pyrimidinyl, 4-pyrimidinyl, 5-pyrimidinyl, 6-pyrimidinyl, 1,2,3-triazol-1-yl, 1,2,3-triazol-4-yl, 1,2,3-triazol-5-yl, 1,2,4-triazol-1-yl, 1,2,3-triazol-3-yl, 1,2,3-triazol-5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-oxadiazol-3-yl, 1,2,4-oxadiazol-5-yl, 1,3,4-thiadiazol-2-yl, 1,3,4-thiadiazol-5-yl, 1,3,4-thiadiazol-3-yl, 1,2,3-thiadiazol-4-yl, 1,2,3-thiadiazol-5-yl, 3-pyridazinyl-, 4-pyridazinyl, 2-pyrazinyl and 3-pyrazinyl or
a substituted or unsubstituted bicyclic heteroaryl group selected from the group consisting of 2-, 3-, 4-, 5-, 6- and 7-benzofuryl, 2-, 3-, 4-, 5-, 6- and 7-benzothienyl, 1-, 2-, 3-, 4-, 5-, 6- and 7-indolyl, 1-, 2-, 3-, 4-, 5-, 6- or 7-isoindolyl, 1-, 2-, 4- and 5-benzimidazolyl, 1-, 3-, 4-, 5-, 6- and 7-benzoxazolyl, 2-, 4-, 5-, 6- and 7-benzoxazolyl, 3-, 4-, 5- 6- and 7-benzothiazolyl, 1-, 3-, 4-, 5-, 6- and 7-benzothiazolyl, 2-, 4-, 5-, 6- and 7-benzisothiazolyl, 2-, 4-, 5-, 6- and 7-benz-1,3-oxadiazolyl, 2-, 3-, 4-, 5-, 6-, 7- and 8-quinolinyl, 1-, 3-, 4-, 5-, 6-, 7-, 8-isoquinolinyl, and 2-, 4-, 5-, 6-, 7- and 8-quinazolinyl.

15. A pharmaceutical composition comprising
a) one or more compounds of formula I of claim 1, or a isolated stereoisomer, a pharmaceutically acceptable salt, or a prodrug of a compound of formula (I) and
b) at least one pharmaceutically acceptable carrier.

16. A pharmaceutical composition comprising
a) one or more compounds of formula I of claim 1, or a salt, prodrug or isolated stereoisomer of a compound of formula I,
b) at least one other cytotoxic or cytostatic chemotherapeutic agent, wherein the amounts of a) and b) are jointly effective for treating a cancer, and
c) at least one pharmaceutically acceptable carrier.

17. A kit comprising a separate dose of a compound of formula I of claim 1, or a salt, prodrug or isolated stereoisomer thereof, and a separate dose of a cytotoxic or cytostatic chemotherapeutic agent in separate containers.

* * * * *